US011419958B2

(12) United States Patent
Bricker et al.

(10) Patent No.: US 11,419,958 B2
(45) Date of Patent: Aug. 23, 2022

(54) FLEXIBLE MULTI-PANEL STERILIZATION ASSEMBLY WITH BOLSTERS

(75) Inventors: Eric T. Bricker, Roswell, GA (US); Jeffrey J. Farmer, Roswell, GA (US); Melissa R. Gaynor, Canton, GA (US); Shawn E. Jenkins, Duluth, GA (US); Mark T. Pamperin, Cumming, GA (US); Corinna Schwarz, Roswell, GA (US); Tara Denise Smith, Marietta, GA (US); Catherine J. Turnbow, Cumming, GA (US)

(73) Assignee: O&M Halyard, Inc., Mechanicsville, VA (US)

( * ) Notice: Subject to any disclaimer, the term of this patent is extended or adjusted under 35 U.S.C. 154(b) by 161 days.

(21) Appl. No.: 13/364,636

(22) Filed: Feb. 2, 2012

(65) Prior Publication Data

US 2012/0202000 A1    Aug. 9, 2012

(51) Int. Cl.
  *A61L 2/26*    (2006.01)
(52) U.S. Cl.
  CPC ........... *A61L 2/26* (2013.01); *A61L 2202/181* (2013.01); *Y10T 428/24008* (2015.01)
(58) Field of Classification Search
  USPC ................ 128/849–857; 602/52, 54, 57, 58
  See application file for complete search history.

(56) References Cited

U.S. PATENT DOCUMENTS

| | | |
|---|---|---|
| 2,997,166 A | 8/1961 | Pratt |
| 3,107,786 A * | 10/1963 | Adelman ............ 206/278 |
| 3,409,121 A | 11/1968 | Taterka |
| 3,616,114 A | 10/1971 | Hamaguchi et al. |
| 3,680,772 A | 8/1972 | Hoover |
| 3,746,152 A | 7/1973 | Allen |
| 3,780,857 A | 12/1973 | Rosano et al. |
| 4,020,842 A | 5/1977 | Richman et al. |
| 4,241,828 A | 12/1980 | Bourdelle et al. |

(Continued)

FOREIGN PATENT DOCUMENTS

| | | |
|---|---|---|
| CN | 1137881 A | 12/1996 |
| EP | 0 754 796 A1 | 1/1997 |

(Continued)

OTHER PUBLICATIONS

Co-pending U.S. Appl. No. 13/196,245 filed Aug. 2, 2011 by Tara Denise Smith et al. for "System for Securing Flexible Multi-Panel Sterilization Assembly".

*Primary Examiner* — Caitlin A Carreiro
(74) *Attorney, Agent, or Firm* — Dority & Manning, P.A.

(57) ABSTRACT

A multi-panel sterilization assembly that includes a barrier panel formed of a permeable material, barrier panel bolsters at or adjacent at least a portion of two edges of the barrier panel, a fold protection panel, and at least one panel attachment means. The barrier panel has a first end and a second end opposite the first end such that the barrier panel has a length that is the distance from the first end to the second end and a midpoint along the length generally delineating the barrier panel into a content receiving region and a content covering region. The barrier panel bolsters prevent the edges of the barrier panel from folding back onto itself, i.e. back towards the unfolded position, during unfolding of the barrier panel after sterilization.

20 Claims, 18 Drawing Sheets

(56) References Cited

U.S. PATENT DOCUMENTS

| | | | |
|---|---|---|---|
| 4,342,392 A * | 8/1982 | Cox | A61F 15/001 |
| | | | 128/855 |
| 4,380,485 A | 4/1983 | Schuster | |
| 4,395,254 A | 7/1983 | Schuster | |
| 4,801,480 A | 1/1989 | Panza et al. | |
| 4,887,615 A | 12/1989 | Taylor | |
| 4,890,628 A * | 1/1990 | Jackson | A61B 46/00 |
| | | | 128/849 |
| 5,035,687 A | 7/1991 | Sandbank | |
| 5,462,540 A | 10/1995 | Caldwell | |
| 5,510,161 A | 4/1996 | Lloyd | |
| 5,698,481 A * | 12/1997 | Van Hout | A61L 2/26 |
| | | | 442/394 |
| 5,922,428 A | 7/1999 | Pufahl | |
| 6,406,674 B1 | 6/2002 | Bourne et al. | |
| 6,578,348 B1 | 6/2003 | Banks | |
| 6,656,171 B1 | 12/2003 | Matsuda et al. | |
| 6,866,928 B2 | 3/2005 | Narum et al. | |
| 8,485,419 B2 | 7/2013 | Gaynor et al. | |
| 2001/0036519 A1 | 11/2001 | Bayer | |
| 2006/0104856 A1 | 5/2006 | Farrell et al. | |
| 2006/0104857 A1 * | 5/2006 | Pigott | A61L 2/26 |
| | | | 422/1 |
| 2007/0095699 A1 | 5/2007 | Frieze et al. | |
| 2007/0128094 A1 | 6/2007 | Paris Jolly et al. | |
| 2008/0237086 A1 * | 10/2008 | Wilson | A61B 50/30 |
| | | | 206/570 |
| 2008/0253947 A2 | 10/2008 | Davis | |
| 2010/0021671 A1 | 1/2010 | Tu | |
| 2010/0262061 A1 | 10/2010 | Fitzgerald et al. | |
| 2011/0033137 A1 | 2/2011 | Gaynor et al. | |
| 2012/0079795 A1 | 4/2012 | Smith et al. | |
| 2013/0001283 A1 | 1/2013 | Friderich et al. | |
| 2013/0081355 A1 | 4/2013 | Gaynor et al. | |
| 2013/0092724 A1 | 4/2013 | Gaynor et al. | |
| 2013/0168441 A1 | 7/2013 | Landgrebe et al. | |
| 2014/0027499 A1 | 1/2014 | Gaynor et al. | |

FOREIGN PATENT DOCUMENTS

| | | |
|---|---|---|
| EP | 1 760 130 A2 | 3/2007 |
| JP | 2000-265132 A | 9/2000 |
| WO | WO 1994/016884 A1 | 8/1994 |
| WO | WO 2004/048665 A2 | 6/2004 |
| WO | WO 2005/037333 A1 | 4/2005 |
| WO | WO 2005/066406 A1 | 7/2005 |
| WO | WO 2006/038978 A1 | 4/2006 |
| WO | WO 2006/055083 A1 | 5/2006 |
| WO | WO 2007/018645 A1 | 2/2007 |
| WO | WO 2008/083426 A1 | 7/2008 |
| WO | WO 2008/108135 A1 | 9/2008 |
| WO | WO 2009/143551 A1 | 12/2009 |
| WO | WO 2010/042847 A1 | 4/2010 |

* cited by examiner

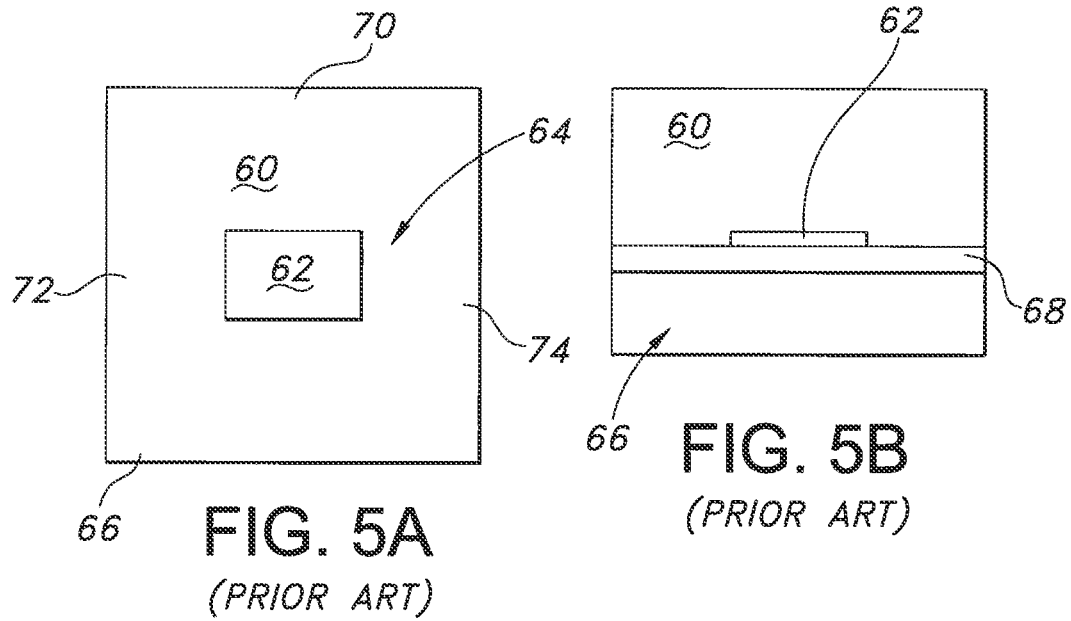
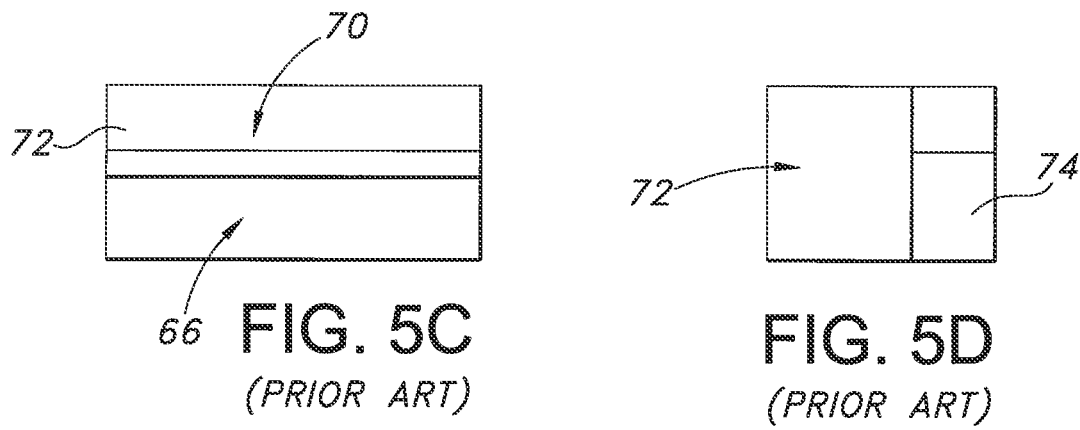
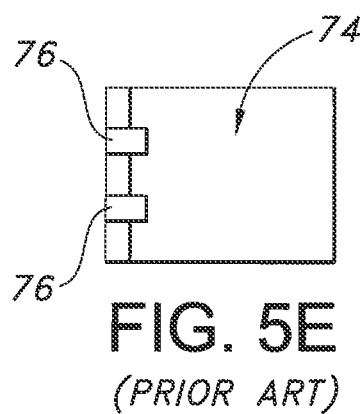

FLEXIBLE MULTI-PANEL STERILIZATION ASSEMBLY WITH BOLSTERS

This application claims priority from provisional U.S. patent application 61/439,683, filed Feb. 4, 2011.

FIELD OF THE INVENTION

The present invention relates in general to disposable wraps used to contain content to be sterilized and store that content aseptically until use.

BACKGROUND OF THE INVENTION

A variety of products such as gowns, sheets, drapes, instruments, etc. which are required during surgery or other aseptic procedures, are used on a daily basis in the normal operation of hospitals, clinics and the like. Where such products are not pre-packaged in a sterile state, it is necessary for the hospital or clinic to sterilize them before use. Furthermore, where these products are not disposable, and are employed more than once, it is necessary that they be cleaned and otherwise prepared for subsequent use. Prior to such use, however, it is essential that such products be sterilized.

Due to the volume of materials involved, it is often necessary to sterilize and store these products for later use. Accordingly, there has been developed a procedure where such products, after cleaning, laundering and the like, are wrapped in sterilization fabric and then sterilized and stored for subsequent use. Disposable sterilization fabric is typically cut into predetermined rectangular shapes and sold as sterilization wraps.

Traditional wrapping of a sterilization tray or similar articles in a conventional disposable sterilization wrap often involves a large amount of redundant material as excess corners and overlapping plies are gathered, folded, and secured together at the top of the sterilization tray.

Conventional disposable sterilization wrap is a flat, featureless sheet of material that may occasionally contain one or more additional layers of material for strength or absorbency. This flat, featureless configuration provides no information or guidance to a person wrapping an article with the flat sheet of material on how to wrap an article.

Conventional disposable sterilization wrap is frequently made of inexpensive, relatively impermeable material such as, for example, paper and the like. The properties of these materials have generally influenced folding techniques and wrapping configurations to ensure the sterility of the wrapped tray or article.

For example, U.S. Pat. No. 5,635,134 to Bourne, et al. discloses a multi-ply sterilization wrap which is formed by joining one or more sheets of sterilization wrap (e.g., two separate sheets or one sheet folded over) together to form two similarly sized, superposed panels that allow convenient dual wrapping of an article. As another example, U.S. Patent Application Publication No. 2001/0036519 by Robert T. Bayer discloses a two ply sterilization wrap that is formed of a single sheet of sterilization wrap material which is folded to form two similarly sized, superposed panels that are bonded to each other. As yet another example, U.S. Patent Application Publication No. 2005/0163654 by Stecklein, et al. discloses a sterilization wrap material that has a first main panel and a second panel that is smaller than the main panel. The second panel is superposed and bonded to the central portion of the main panel such that it is contained entirely within the main panel to reinforce the main panel and/or provide additional absorbency.

Generally speaking, in these and other examples, large sheets of conventional disposable sterilization wrap are typically used to create large expanses of overlapping materials using one or two standard fold techniques. These conventional techniques and the resulting fold configurations require manipulating excess amount of materials during the wrapping and unwrapping process. It takes experience and a certain level of skill to wrap a tray or similar article quickly and reliably. Because of scheduling and cost pressures, medical equipment needed for some procedures may require immediate turnaround and must be processed, sterilized and available for use within hours of its use in a previous procedure. As turnaround times continue to compress, there is a corresponding increase in the need to wrap an article even more quickly while ensuring the integrity of the wrapping. There is also a corresponding increase in the need to quickly unwrap a sterilized article while preserving the sterility of the sterilized article.

Large sheets of conventional disposable sterilization wrap in combination with standard fold techniques do provide an advantage during unwrapping of an item after sterilization, particularly when the sterilization wrap is formed from a material that may stiffen or take a set during the sterilization process. For example, when sterilization wrap composed of nonwoven material made from certain thermoplastic polymers are used in an extended or enhanced steam or heat sterilization process, the nonwoven material may set or "imprint" the shape of the wrapped article or tray. During unwrapping of the article or tray, imprinted creases, folds or other deformations must be overcome during unfolding so the sterilization wrap can lay flat. If the sterilization wrap does not lie flat, it is possible for unfolded sides of the sterilization wrap to fold back up over the sterilized article or tray while other portions of the wrap are being unfolded. This would compromise the sterility of the article. The large expanses of material and the square shape of the sheets in combination with standard folding techniques generally keep the sterilization wrap from folding back onto itself during unwrapping.

The problem of unfolded sides of the sterilization wrap folding back up over the sterilized article or tray while other portions of the wrap are being unfolded is made worse when these large sheets of conventional sterilization wrap are reduced in size. Moreover, this problem can also be amplified by altering the geometry of the sheet of sterilization wrap so the sheet is no longer square (e.g., in order to reduce the amount of material in the sheet). However, the use of large sheets of conventional disposable sterilization wrap with standard fold techniques provides large expanses of overlapping materials and multiple folds which require using and manipulating excessive amounts of material during the wrapping and unwrapping process, adding difficulty that slows the wrapping and unwrapping process, and creating waste.

Accordingly, there is an unmet need for an easy to use assembly, package or system that reduces the amount of sterilization fabric needed for the sterile processing of an instrument tray or article. There is also an unmet need for an easy to use assembly, package or system that reduces the amount of sterilization fabric and simplifies the task of unwrapping a sterilized instrument tray or article while reducing or avoiding the likelihood that the sterilization fabric will fold back onto itself during unwrapping. The need is particularly apparent for an assembly, package or system that reduces the amount of sterilization fabric, that can be used in an extended or enhanced steam or heat sterilization process, and that simplifies the task of unwrapping a sterilized instrument tray or article while reducing or avoiding the likelihood that the sterilization fabric will fold back onto itself during unwrapping.

SUMMARY

The problems described above are addressed by the present invention which encompasses a disposable flexible multi-panel sterilization assembly. The disposable flexible multi-panel sterilization assembly includes a barrier panel composed of a permeable sheet material having barrier properties, barrier panel bolsters that prevent the barrier panel from folding back on itself during unfolding of the barrier panel; panel attachment means for securing the barrier panel into a package; and a fold protection panel.

The barrier panel includes: a first surface and a second opposing surface; a first end generally defining a pre-determined fold line; a second end opposite the first end; a first edge that is generally perpendicular to the pre-determined fold line; a second edge that is generally opposite the pre-determined fold line; and a third edge that is generally perpendicular to the pre-determined fold line. Desirably, the barrier panel may have a fourth edge that is located generally opposite the pre-determined fold line such that the second edge and the fourth edge form an apex or vertex. More desirably, the barrier panel may have a fourth edge and a fifth edge to define a non-square or non-rectangular shape such that, for example, the fourth edge and a fifth edge generally converge toward the second edge such that the second end of the barrier panel is narrower than the first end of the barrier panel.

The barrier panel may have a width that is the distance from the first edge to the third edge and a length that is the distance from the first end to the second end. According to an aspect of the invention, the barrier panel has a midpoint along the length which spans or runs between the first edge and the third edge to generally delineate the barrier panel into a content receiving region extending from the pre-determined fold line to the midpoint and a content covering region extending from the midpoint to the second edge. According to an aspect of the invention, the surface area of the content receiving region may be from about 25 percent to about 49 percent of the total surface area of the barrier panel. For example, the surface area of the content receiving region may be from about 35 percent to about 45 percent of the total surface area of the barrier panel.

The barrier panel bolsters are located at or adjacent the first and third edges of the barrier panel and extend inwardly from those edges, overlaying the barrier panel. These barrier panel bolsters prevent the first and third edges of the barrier panel from folding back on itself, i.e., back towards the unfolded position, during unfolding of the barrier panel, particularly after extended steam or heat sterilization. The barrier panel bolsters can be located at or adjacent the first and third edges of the content covering region of the barrier panel. The barrier panel bolsters may provide reinforcement to the barrier panel. The barrier panel bolsters may extend into the content receiving portion of the barrier panel. For example, the barrier panel bolsters may provide reinforcement to the barrier panel in the content receiving portion and define an area for receiving content to be sterilized. In an aspect of the invention, the barrier panel bolsters increase the basis weight of the barrier panel by more than 5 percent at or adjacent the edges of the barrier panel. For example, the barrier panel bolsters may increase the basis weight of the barrier panel by 10 percent to about 75 percent at or adjacent the edges of the barrier panel. In another aspect of the invention, the attachment of the bolsters may stiffen the barrier panel at or adjacent the edges of the barrier panel at least about 5 percent more than the combined stiffness of the unattached bolsters and barrier panel. For example, the attachment of the bolsters may stiffen the barrier panel at or adjacent the edges of the barrier panel 10% to about 75% more than the combined stiffness of the unattached bolsters and barrier panel. The barrier panel bolsters may be one or more materials or layers of material selected from fibrous webs, textiles, films and combinations thereof. For example, the barrier panel bolster may be a layer or layers of non-woven material that is joined to the barrier panel by adhesives, thermal bonding, ultrasonic bonding or other techniques.

The multi-panel sterilization assembly includes a panel attachment means located between the pre-determined fold line and the midpoint of the barrier panel. The panel attachment means is desirably at or near the first edge or the third edge of the barrier panel. Desirably, the panel attachment means may be at or near both the first edge and the third edge of the barrier panel and may be used to attach the barrier panel to itself after the barrier panel is folded around content to be sterilized to form a package. In an aspect of the invention, the panel attachment means may be located in close proximity to the first edge and the third edge of the barrier panel and/or may extend from the first edge and the third edge of the barrier panel. The panel attachment means may be adhesive tape, double-sided adhesive tape, cleavable release tapes, layered release tapes, cohesive materials, hook and loop fastening systems, mechanical fastening systems including, but not limited to, snaps, clips, magnets, catches, slots and tabs, and combinations thereof. According to an aspect of the invention, the panel attachment means is joined to the barrier panel at a pre-determined position. This pre-determined position may near the pre-determined fold line. The panel attachment means may be configured to identify the barrier panel's content receiving region and further to join the barrier panel's first edge and third edge to each other or to a portion of the content covering region after the barrier panel has been folded at or near its midpoint such that its second end is brought near its first end.

The multi-panel sterilization assembly further includes a fold protection panel in juxtaposed communication with the barrier panel. That is, the fold protection panel desirably extends from the barrier panel. If the fold protection panel is a separate piece of material, it is desirably immediately adjacent the barrier panel in side-by-side relationship. The fold protection panel includes: a proximal end generally adjacent or adjoining the pre-determined fold line; a distal end generally opposite the proximal end; and at least a first edge and a second edge extending from the proximal end to the distal end. According to the present invention, the fold protection panel may have at least a third edge located at or along its distal end. The fold protection panel may be configured so it has barrier properties. For example, the fold protection panel may be formed of the same material as the barrier panel. As another example, the fold protection panel may be formed of the same piece of material as the barrier panel.

In an aspect of the invention, the fold protection panel desirably has a width that is the distance from the first edge to the second edge and a length that is the distance from the proximal end to the distal end, such that, after the barrier panel has been folded at or near the barrier panel's midpoint, the barrier panel's second end is brought near its first end and its first and third edges are joined to each other or to its content covering region to form a package, the fold protection panel is configured to fold at or near the pre-determined fold line to cover at least the first edge and the third edge of the folded barrier panel.

According to the present invention, the barrier panel may be composed of at least one layer of a breathable nonwoven material. Desirably, the breathable nonwoven material is a laminate composed of a layer of spunbonded filaments, a layer of meltblown fibers, and a layer of spunbonded filaments. The permeability of the barrier panel may range from 25 to about 500 cubic feet per minute (CFM) as characterized in terms of Frazier permeability. For example, the permeability of the barrier panel may range from 25 to about 400 cubic feet per minute. As yet another example, the permeability of the barrier panel may range from 25 to about 300 cubic feet per minute.

The sterilization assembly further includes at least one pull tab. The pull tab may be unitary with the barrier panel or it may be attached to the second end of the barrier panel. The pull tab may be formed of the same material as the barrier panel or may be formed of one or more different materials. The pull tab provides a feature that allows a user to unwrap a sterilized article aseptically. That is, a person unwrapping an article that is folded in the flexible multi-panel sterilization assembly may use the pull tab to avoid reaching over the sterile field generally presented from unwrapping and spreading out the sterile content-contacting surface of the barrier panel.

The sterilization assembly may further include one or more discrete reinforcement elements. These elements are desirably in the content receiving region that define an area for receiving content to be sterilized. The reinforcement element(s) may include one or more layers of materials selected from fibrous webs, impermeable films, permeable or porous films, apertured films, foams, foils and combinations thereof.

According to an aspect of the invention, the sterilization assembly may further include indicia or instructions on the sterilization assembly itself to inform the proper folding of the assembly into a package. Alternatively and/or additionally, the sterilization assembly may further include indicia or instructions on the sterilization assembly itself to inform the proper unfolding or unwrapping of the assembly after it has been folded into a package and sterilized.

In an aspect of the invention, there is provided a disposable flexible multi-panel sterilization assembly that includes a barrier panel formed from a sheet of barrier material (e.g., barrier fabric) having at least two panel edges. The barrier panel is configured to be folded around content to be sterilized to form a package. Barrier panel bolsters are located at or adjacent at least a portion of at least two panel edges of the barrier panel. Barrier panel attachment means are located on a portion of the barrier panel for securing one or more panel edges of the barrier panel in a folded configuration around content to be sterilized. The barrier panel attachment means are configured to secure the one or more panel edges in a folded configuration with substantially greater resistance to shear force than to peel force. The multi-panel sterilization assembly further includes a fold protection panel extending from the barrier panel. The fold protection panel includes a proximal end generally adjacent the barrier panel and a distal end generally opposite the proximal end such that the distal end of the fold protection panel covers the one or more panel edges of the barrier panel after the barrier panel is in the folded configuration and the barrier panel bolsters prevent the edges of the barrier panel from folding back on itself during unfolding of the barrier panel.

The barrier panel bolsters may provide reinforcement to the barrier panel and/or define an area for receiving content to be sterilized. The barrier panel bolsters may increase the basis weight of the barrier panel by more than 5 percent at or adjacent the edges of the barrier panel. Alternatively and/or additionally, the attachment of the bolsters may stiffen the barrier panel at or adjacent the edges of the barrier panel at least about 5 percent more than the combined stiffness of the unattached bolsters and barrier panel. The barrier panel bolsters may be one or more materials or layers of material as described above.

The barrier panel attachment means are used to attach the barrier panel to itself after the barrier panel is folded around content to be sterilized to form a package. The barrier panel attachment means may be adhesive tape, double-sided adhesive tape, cleavable release tapes, cohesive materials, hook and loop fastening systems, mechanical fastening systems including, but not limited to, snaps, clips, magnets, catches, slots and tabs, and combinations thereof.

These and other features and advantages of the invention will become more apparent to one skilled in the art from the following description and claims when read in light of the accompanying drawings.

BRIEF DESCRIPTION OF THE DRAWINGS

The present invention will be better understood by reading the Detailed Description of the Invention with reference to the accompanying drawing figures, in which like reference numerals denote similar structure and refer to like elements throughout, and in which:

FIGS. 5A to 5E are illustrations of an exemplary sequence of folding an exemplary prior art sterilization wrap system using a conventional square fold.

DEFINITIONS

Figure 1:
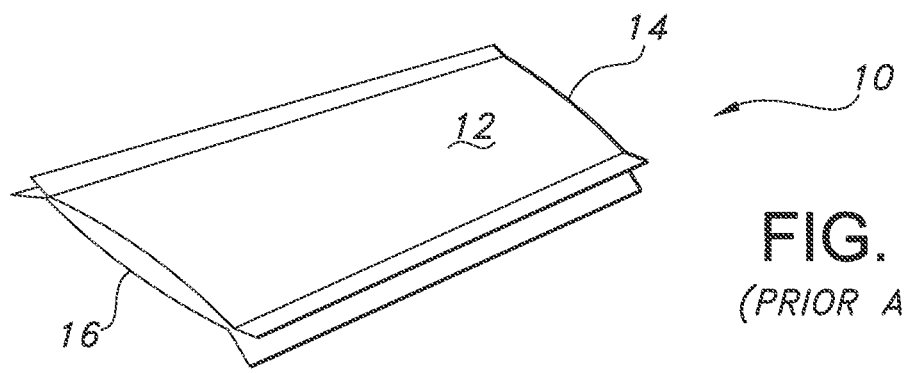
FIG. 1 is an illustration of an exemplary prior art sterilization wrap system.

As used herein, the term "disposable" refers to a product that is so inexpensive that it may economically be discarded after only a single use. Products that are "disposable" are typically intended for single use. The term "single-use" refers to a product that is intended to be used for only once and is not intended to be re-used, re-conditioned, restored or repaired after that use. These products offer advantages in clinical settings by reducing the potential for contamination or infection. In addition, these products can enhance work flow since they are not collected and assembled for reprocessing and reuse.

As used herein, the term "sterilization assembly" refers to a flexible article composed of fabric(s) and/or flexible material(s) that is wrapped around, folded around or otherwise encloses a non-sterile article or non-sterile content prior to sterilization. A sterilization assembly has multiple panels and/or sections providing specific physical properties, functional characteristics and/or structure that provide advantages for wrapping or folding, handling, strength, sterilization, storage after sterilization, and/or unwrapping or unfolding.

As used herein, the term "nonwoven web" refers to a web that has a structure of individual fibers or filaments which are interlaid, but not in an identifiable repeating manner.

Nonwoven webs have been, in the past, formed by a variety of processes known to those skilled in the art such as, for example, meltblowing, spunbonding and bonded carded web processes.

As used herein, the term "spunbonded web" refers to a web of small diameter fibers and/or filaments which are formed by extruding a molten thermoplastic material as filaments from a plurality of fine, usually circular, capillaries in a spinnerette with the diameter of the extruded filaments then being rapidly reduced, for example, by non-eductive or eductive fluid-drawing or other well known spunbonding mechanisms. The production of spunbonded nonwoven webs is illustrated in patents such as Appel, et al., U.S. Pat. No. 4,340,563; Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; and Harmon, Canadian Patent No. 803,714.

As used herein, the term "meltblown fibers" means fibers formed by extruding a molten thermoplastic material through a plurality of fine, usually circular, die capillaries as molten threads or filaments into a high-velocity gas (e.g. air) stream which attenuates the filaments of molten thermoplastic material to reduce their diameters, which may be to microfiber diameter. Thereafter, the meltblown fibers are carried by the high-velocity gas stream and are deposited on a collecting surface to form a web of randomly disbursed meltblown fibers. The meltblown process is well-known and is described in various patents and publications, including NRL Report 4364, "Manufacture of Super-Fine Organic Fibers" by V. A. Wendt, E. L. Boone, and C. D. Fluharty; NRL Report 5265, "An Improved device for the Formation of Super-Fine Thermoplastic Fibers" by K. D. Lawrence, R. T. Lukas, and J. A. Young; and U.S. Pat. No. 3,849,241, issued Nov. 19, 1974, to Buntin, et al.

As used herein, "ultrasonic bonding" means a process performed, for example, by passing the fabric between a sonic horn and anvil roll as illustrated in U.S. Pat. No. 4,374,888 to Bornslaeger, the entire contents of which is incorporated herein by reference.

As used herein "point bonding" means bonding one or more layers of fabric at a plurality of discrete bond points. For example, thermal point bonding generally involves passing a fabric or web of fibers to be bonded between a heated roll assembly such as, for example, a heated calender roll and an anvil roll. The calender roll is usually patterned in some way so that the entire fabric is not bonded across its entire surface, and the anvil roll is usually smooth. As a result, various patterns for calender rolls have been developed for functional and/or aesthetic reasons. One example of a pattern has points and is the Hansen Pennings or "H&P" pattern with about a 30% bond area with about 200 bonds/square inch (31 bonds/square cm) as taught in U.S. Pat. No. 3,855,046 to Hansen and Pennings. Another example is shown in U.S. Design Pat. No. 239,566 to Vogt. Typically, the percent bonding area varies from around 5% to around 30% of the area of the fabric laminate web. Spot bonding holds the laminate layers together as well as imparts integrity to each individual layer by bonding filaments and/or fibers within each layer without destroying the breathability or hand of the fabric.

DETAILED DESCRIPTION

In describing the various embodiments of the present invention, as illustrated in the figures and/or described herein, specific terminology is employed for the sake of clarity. The invention, however, is not intended to be limited to the specific terminology so selected, and it is to be understood that each specific element includes all technical equivalents that operate in a similar manner to accomplish similar functions.

Referring now to FIG. 1, there is shown an exemplary conventional disposable sterilization wrap 10 having a multiple-ply configuration which is formed by joining one or more sheets 12 of sterilization wrap together to form two similarly sized, superposed panels 14 and 16 that allow convenient dual wrapping of an article. While one sheet may be folded back on itself to provide the multiple-ply configuration, two separate sheets are more typically used.

Figure 2:
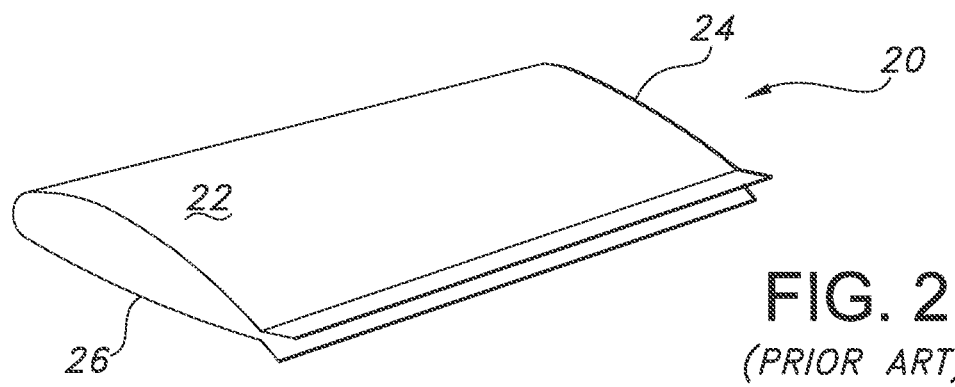
FIG. 2 is an illustration of an exemplary prior art sterilization wrap system.

FIG. 2 is an illustration of an exemplary conventional disposable sterilization wrap 20 as generally disclosed in U.S. Patent Application Publication No. 2001/0036519 by Robert T. Bayer. The conventional disposable sterilization wrap 20 is a two ply sterilization wrap formed of a single sheet 22 of sterilization wrap material which is folded to form two similarly sized, superposed panels 24 and 26 that are bonded to each other.

Figure 3:
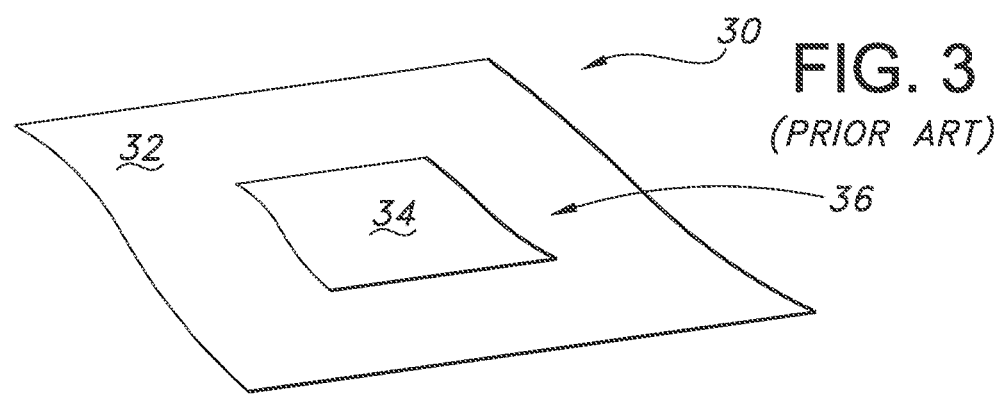
FIG. 3 is an illustration of an exemplary prior art sterilization wrap system.

FIG. 3 is an illustration of yet another example of a conventional disposable sterilization wrap 30 as generally disclosed in U.S. Patent Application Publication No. 2005/0163654 by Stecklein, et al. The conventional disposable sterilization wrap 30 has a first main panel 32 and a second panel 34 that is much smaller than the main panel 32. The second panel 34 is superposed and bonded to the central portion 36 of the main panel 32 to reinforce the main panel 32 and/or provide additional absorbency.

Generally speaking, in these and other examples, large sheets of conventional disposable sterilization wrap are typically used to create large expanses of overlapping materials using one or two standard fold techniques. These standard techniques and the resulting fold configurations require manipulating excess amount of materials during the wrapping and unwrapping process. It takes experience and a minimum level of skill to reliably wrap a tray or similar article quickly.

Figures 4A, 4B:
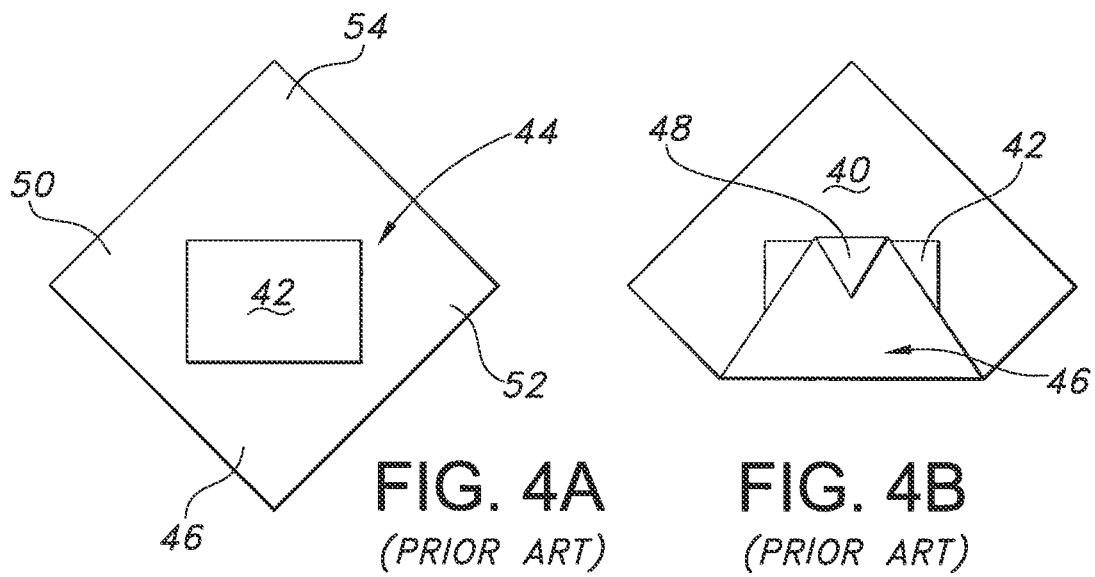
FIGS. 4A to 4E are illustrations of an exemplary sequence of folding an exemplary prior art sterilization wrap system using a conventional envelope fold.
Figures 4C, 4D:
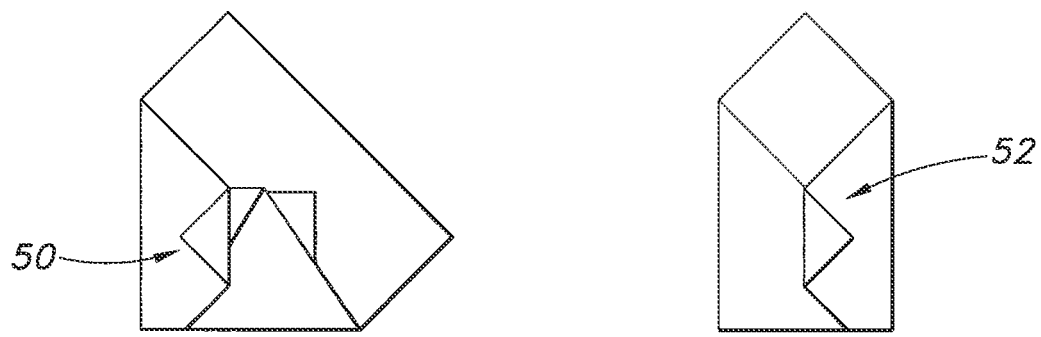
Figure 4E:
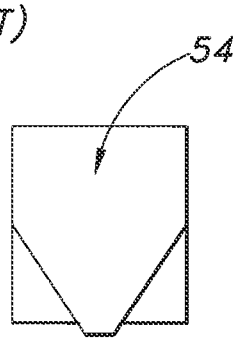

FIGS. 4A through 4E illustrate an exemplary sequence of steps in wrapping an article utilizing a conventional sterilization wrap. As illustrated in FIG. 4A, a square or generally rectangular wrap 40 is spread out flat and an article 42 to be wrapped is placed in a central region 44 of the wrap 40 in a generally diagonal relationship to the orientation of the wrap 40 in a pattern conventionally referred to as an envelope fold. Referring to FIG. 4B, a first end 46 of the wrap is folded up at the base of the article 42 and brought over the article 42. Generally speaking, the sterilization wrap must be sufficiently large in area to provide enough material to substantially cover the article in the initial fold. The first folded end 46 is back-folded to create a small tail 48. This sequence is generally repeated for the remaining second end 50 and the third end 52. Again, the sterilization wrap must be sufficiently sized in area to provide enough material for the second end 50 and the third end 52 to substantially overlap such that the entire or substantially the entire second end 50 is covered by the third end 52. The fourth end 54 is folded over and taped to form a wrapped package.

FIGS. 5A through 5E illustrate an exemplary sequence of steps in wrapping an article utilizing a conventional sterilization wrap. As illustrated in FIG. 5A, a square or generally rectangular wrap 60 is spread out flat and an article 62 to be wrapped is placed in a central region 64 of the wrap 60 in a generally parallel relationship to the orientation of the wrap 60 in a pattern conventionally referred to as a square fold. Referring to FIG. 5B, a bottom end 66 of the wrap is folded up at the base of the article 62 and brought over the article 62. Generally speaking, the sterilization wrap must be sufficiently large in area to provide enough material to substantially cover the article in the initial fold. The folded bottom end 66 is back-folded to create a small tail 68. This sequence is generally repeated for the remaining top end 70 and the left side end 72. Again, the sterilization wrap must be sufficiently sized in area to provide enough material for the top end 70 and the left side end 72 to substantially overlap such that the entire or substantially the entire bottom end 70 is covered by the left side end 72. The right side end 74 is folded over and taped 76 to form a wrapped package.

A typical sterilization tray with the dimensions of 10 inches (25.4 cm) by 20 inches (50.8 cm) by 5 inches tall (12.7 cm) typically requires a square piece of sterilization fabric having each side measuring 45 inches for wrapping and sterile processing. This large size piece is needed so that the corner of the fabric can be folded all the way across the top of the tray with some additional excess material so that the preparer of the tray feels confident that the contents are covered and that the piece of fabric will stay down and not spring back. Using a 45 inch square piece of fabric means that 2025 square inches of material (approximately 13,064 square centimeters) is being used to enclose a tray with a surface area of just 700 square inches (approximately 4,516 square centimeters). In other words, this traditional method requires almost three square inches of material to cover every square inch of a tray of surgical instruments.

Figure 6:
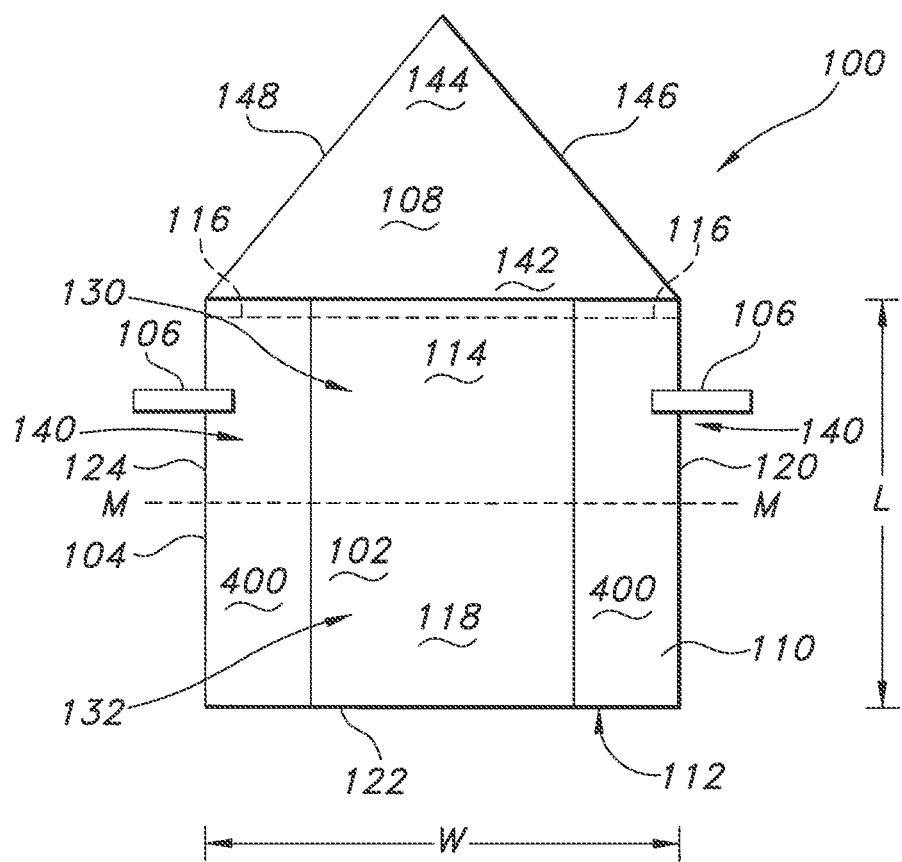
FIG. 6 is an illustration of an exemplary disposable flexible multi-panel sterilization assembly including barrier panel bolsters.

The present invention encompasses a disposable multi-panel sterilization assembly which addresses the problems generally described above and which also addresses a problem discovered when the dimensions of the sterilization fabric are reduced—namely the sterilization fabric can fold back on itself during unfolding of the sterilization fabric. An exemplary multi-panel sterilization assembly 100 is illustrated in FIG. 6.

The multi-panel sterilization assembly includes a barrier panel 102 composed of a permeable sheet material 104 having barrier properties (e.g., a barrier fabric), panel attachment means 106 for securing the barrier panel 102 into a package; and a fold protection panel 108. Generally speaking, the "barrier panel" is the portion of a multi-panel sterilization assembly that is formed from a material that is sufficiently permeable to permit a sterilizing gas to pass through it to effect sterilization and has barrier properties sufficient maintain that content in an aseptic condition after sterilization. A barrier panel should also be sufficiently flexible or conformable to that it is configured to receive and subsequently enfold or enclose content to be sterilized thereby forming a package. Generally speaking, the barrier panel may be a barrier fabric. The "fold protection panel" is the portion of a multi-panel sterilization assembly that is formed from a material that covers and protects at least a portion of the folded edges of the barrier panel. The fold protection panel is the last panel or part of the multi-panel sterilization assembly that is folded or wrapped around the package formed by the barrier panel around content to be sterilized and the first part of the multi-panel sterilization assembly that is unfolded or unwrapped.

The barrier panel includes: a first surface 110 and a second opposing surface 112; a first end 114 generally adjacent or adjoining a pre-determined fold line 116; a second end 118 opposite the first end 114; a first edge 120 that is generally perpendicular to the pre-determined fold line 116; a second edge 122 that is generally opposite the pre-determined fold line 116; and a third edge 124 that is generally perpendicular to the pre-determined fold line 116. The "pre-determined fold line" is a line or region generally defined by the first end 114 of the barrier panel. Generally speaking, the predetermined fold line is offset from the boundary or transition between the barrier panel and the fold protection panel towards the center or midpoint of barrier panel 102. The pre-determined fold line 116 identifies the desired location for placing the content to be sterilized at the first end 114 of the barrier panel 102. The offset serves to provide a sufficient amount of barrier panel that the content to be sterilized is fully surrounded by the barrier panel after folding is complete. The pre-determined fold line 116 may be offset from the boundary or transition by about 0.5 inch (~13 mm) to about 2 inches (~51 mm). Desirably, the pre-determined fold line is offset by about 1 inch (~25 mm). The pre-determined fold line may be in the form of a seam (or seams) such as, for example, a stitched seam, an ultrasonic bond seam, adhesive bond seam, thermo-mechanical bond seam (e.g., a bar seal seam) or combinations thereof, that results from joining layers or plies together to form the barrier panel and the fold protection panel—or the seam(s) may result from joining pieces together if the barrier and fold protection panels are discrete pieces. Alternatively and/or additionally, the predetermined fold line may be identified by printing, or by an imprint such as a thermo-mechanical bond line (e.g., bar seal bond line) or pattern or other indicia, or identified by a crease or other suitable mark. The pre-determined fold line may be an intermittent line or indicia and it may be provided directly on the barrier panel or it may be provided on one or reinforcement elements if such are present.

As noted above, an important feature of the predetermined fold line 116 is that it helps delineate where the content to be wrapped and ultimately sterilized should be placed. That is, content to be wrapped and sterilized should be placed adjacent only one side of the predetermined fold line. As discussed subsequently, other features of the present invention signal to a user which side of the pre-determined fold line is the appropriate side to place content. Yet another feature of the predetermined fold line 116 is that it helps defines a boundary, reference line or limit for the user during the wrapping of content to be sterilized. That is, during wrapping of content to be sterilized, as part of the barrier panel is brought over the content to be sterilized, that part of the barrier panel should not be extended substantially across or beyond the predetermined fold line 116. In contrast to conventional sterilization wrap systems where the content is placed at the center of the sterilization barrier, the multi-panel sterilization assembly required placement at the pre-determined fold line near the boundary or edge of the barrier panel. This is initially counterintuitive for users and is quite different from conventional sterilization wrap systems.

While the barrier panel 102 of FIG. 6 is generally shown as having a square shape, the barrier panel 102 may be rectangular or may desirably have additional edges to define a non-square or non-rectangular shape. Portions of the edges may be arcuate or may otherwise be non-linear. Alternatively and/or additionally, the first edge 120 and the third edge 124 may converge or diverge so the edges are not parallel, thereby defining a barrier panel 102 having a trapezoidal shape. It is also contemplated that other combinations of opposite edges may converge or diverge.

Figure 7A:
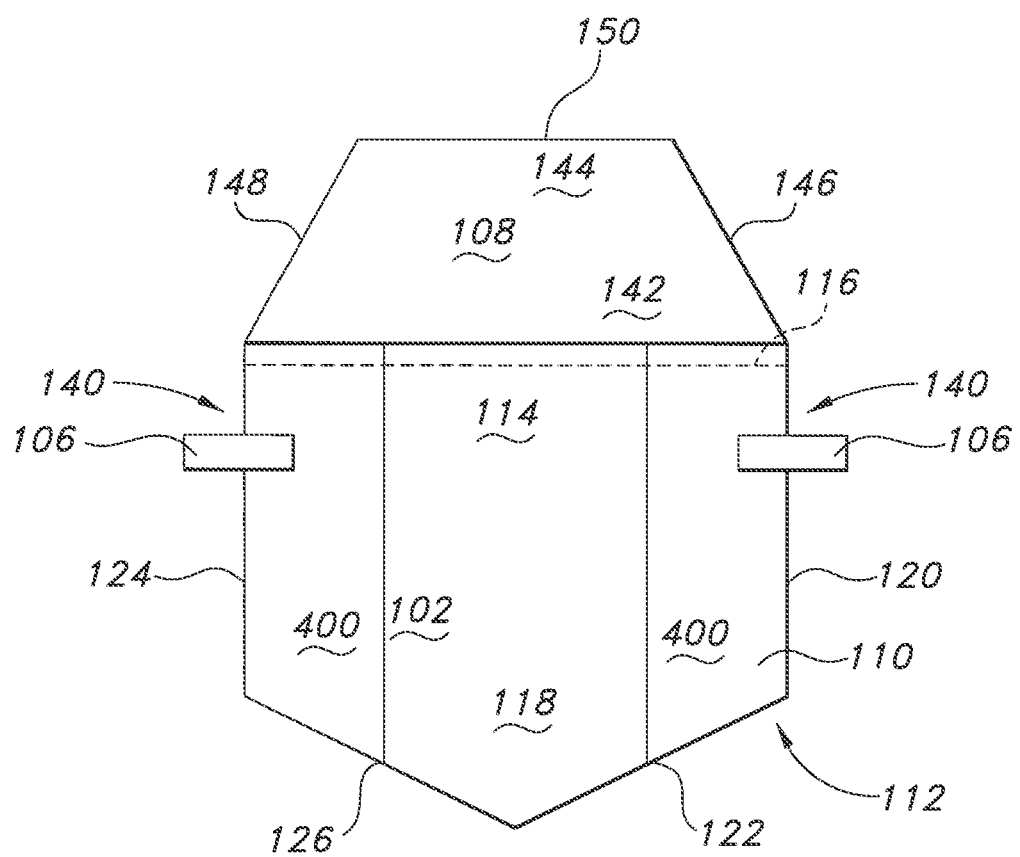
FIG. 7A is an illustration of an exemplary disposable flexible multi-panel sterilization assembly including barrier panel bolsters.

For example and referring to FIG. 7A, the barrier panel may have a fourth edge 126 to define a non-square or non-rectangular shape. In such an exemplary configuration, the two edges 122 and 126 are generally opposite the pre-determined fold line 116 such that the second edge 122 and the fourth edge 126 form an apex or vertex. Thus, the barrier panel 102 may have a first surface 110 and a second opposing surface 112; a first end 114 generally defining a pre-determined fold line 116; a second end 118 opposite the first end 114; a first edge 120 that is generally perpendicular to the pre-determined fold line 116; a second edge 122 that is generally opposite the pre-determined fold line 116; a third edge 124 that is generally perpendicular to the pre-determined fold line; and a fourth edge 126 located between the second edge 122 and the third edge 124.

Figure 8A:
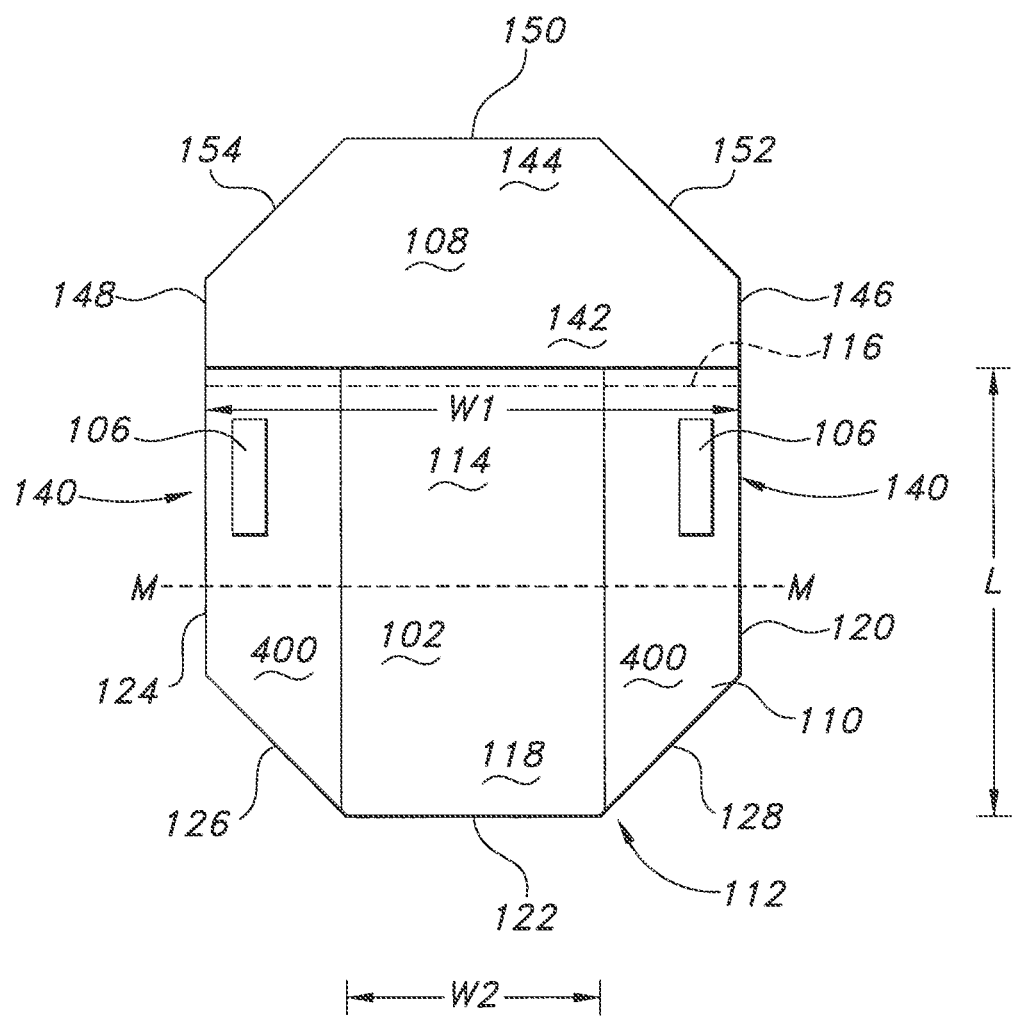
FIG. 8A is an illustration of an exemplary disposable flexible multi-panel sterilization assembly including barrier panel bolsters.
Figure 8B:
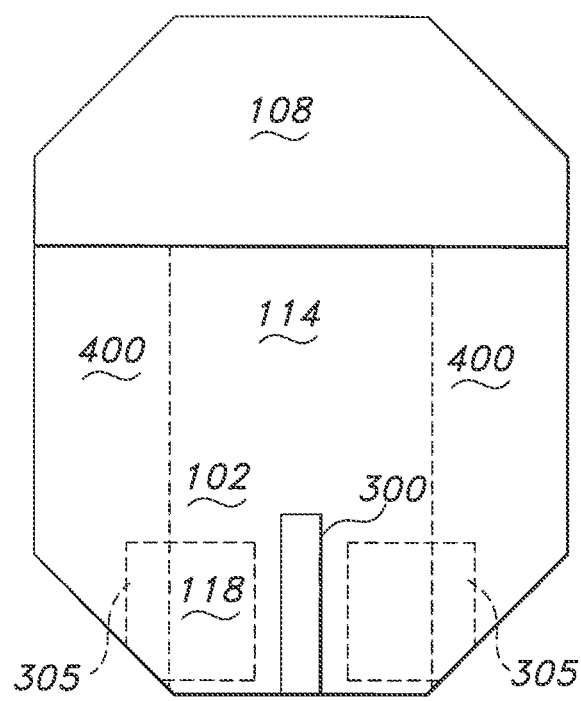
FIG. 8B is an illustration showing the opposite side of the exemplary disposable flexible multi-panel sterilization assembly of FIG. 8A and illustrating optional barrier panel bolsters.

Referring to FIGS. 8A and 8B, the barrier panel 102 may have a fourth edge 126 and a fifth edge 128 to define a non-square or non-rectangular shape such that, for example, the fourth edge 126 and a fifth edge 128 generally converge toward the second edge 226 such that the second end 118 of the barrier panel is narrower than the first end 114 of the barrier panel. Thus, the barrier panel 102 may have a first surface 110 and a second opposing surface 112; a first end 114 generally defining a pre-determined fold line 116; a second end 118 opposite the first end 114; a first edge 120 that is generally perpendicular to the pre-determined fold line; a second edge 122 that is generally parallel to the pre-determined fold line 116; a third edge 124 that is generally perpendicular to the pre-determined fold line 116; a fourth edge 126 located between the second edge 122 and the third edge 124; and, a fifth edge 128 located between the first edge 120 and the second edge 122. The barrier panel has a first width "W1" that is the distance from the first edge 120 to the third edge 124 in the first end 114 (e.g., preferably measured along the pre-determined fold line 116) and a second width "W2" that is the distance from the fourth edge 126 to the fifth edge 128 (e.g., preferably measured between the locations where the fourth edge 126 and the fifth edge 128 meet the second edge 122. The barrier panel also has a length "L" that is the distance from the first end 114 (from the pre-determined fold line 116) to the second end (e.g., at the second edge 122). The barrier panel also has a midpoint "M" along the length "L" and extending between the first edge 120 and the third edge 124 or, in some embodiments, the fourth edge 126 and the fifth edge 128 to generally delineate the barrier panel 102 into a content receiving region 130 extending from the pre-determined fold line 116 to the midpoint "M" and a content covering region 132 extending from the midpoint "M" to the second edge 122". Of course, it is contemplated that additional edges may be added or that edges may be curvilinear or may include curvilinear portions.

Referring again to FIG. 6, the barrier panel 102 may have a width "W" that is the distance from the first edge 120 to the third edge 124 and a length "L" that is the distance from the first end 114 to the second end 118. According to an aspect of the invention, the barrier panel has a midpoint "M" along the length "L" which spans or runs between the first edge 120 and the third edge 124 to generally delineate the barrier panel 102 into a content receiving region 130 extending from the pre-determined fold line 116 to the midpoint "M" and a content covering region 132 extending from the midpoint "M" to the second edge 124. Generally speaking the content receiving region is the portion of the barrier panel onto which a tray or other content to be sterilized is initially placed. Unlike conventional sterilization wrap in which a tray or content to be sterilized is placed in the central portion of the barrier material that forms the sterilization wrap, the content receiving region is between the first end and the midpoint of the barrier panel. This asymmetric placement on the barrier panel is not intuitive. The content covering region is the portion of the barrier panel that is folded over the content after the content has been placed on the content receiving region.

In an aspect of the invention, the barrier panel of the various illustrated configurations may have a width of from about 12 inches (~30 cm) to about 50 inches (~127 cm). Desirably, the barrier panel may have a width of from about 18 inches (~46 cm) to about 40 inches (~102 cm). Even more desirably, the barrier panel may have a width of from about 20 inches (~51 cm) to about 30 inches (~76 cm). The barrier panel may have a length of from about 7 inches (~18 cm) to about 50 inches (~127 cm). Desirably, the barrier panel may have a length of from about 15 inches (~39 cm) to about 40 inches (~102 cm). Even more desirably, the barrier panel may have a length of from about 25 inches (~64 cm) to about 30 inches (~76 cm).

According to an aspect of the invention, the surface area of the content receiving region 130 may be from about 25 percent to about 49 percent of the total surface area of the barrier panel 102. For example, the surface area of the content receiving region 130 may be from about 35 percent to about 45 percent of the total surface area of the barrier panel 102. This is important because the content covering portion of the barrier panel should be larger to provide additional surface area to properly cover the content.

Figure 8C:
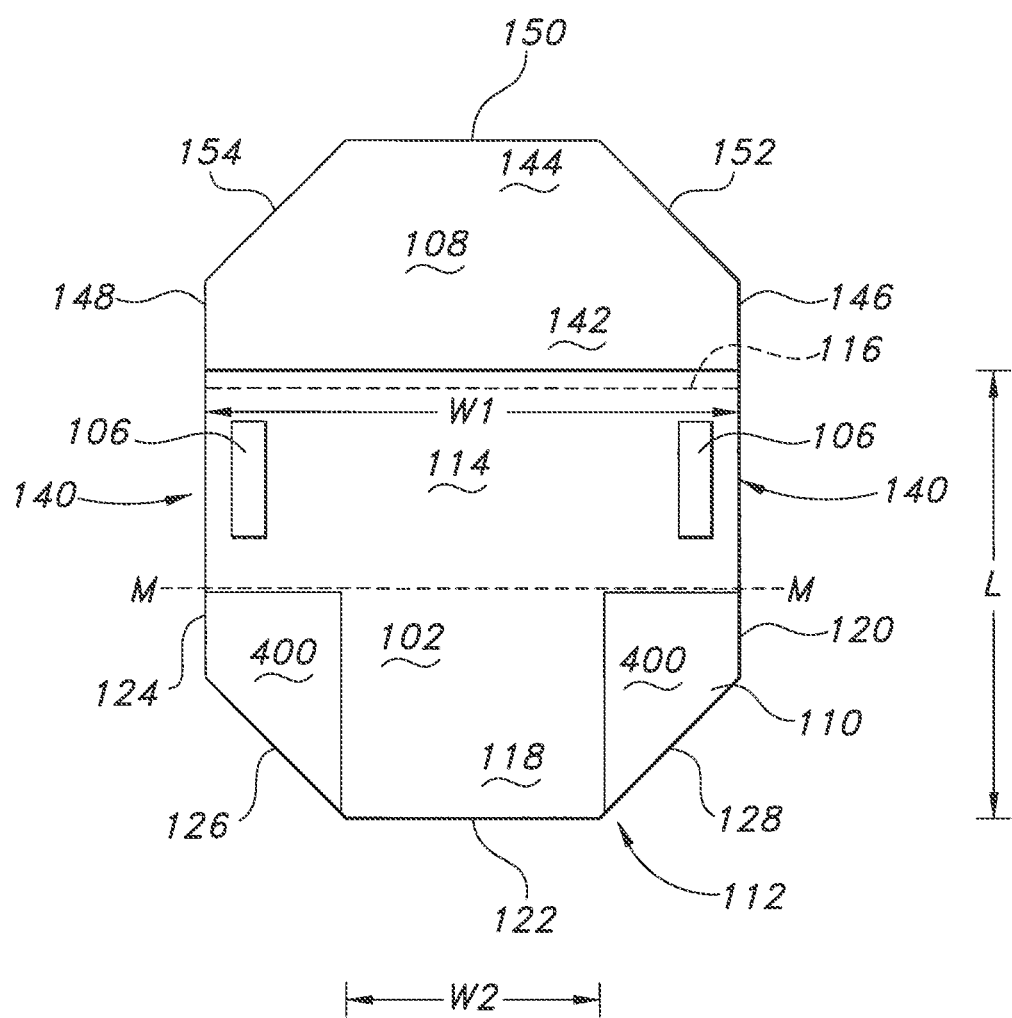
FIG. 8C is an illustration of an exemplary disposable flexible multi-panel sterilization assembly including barrier panel bolsters.
Figure 8D:
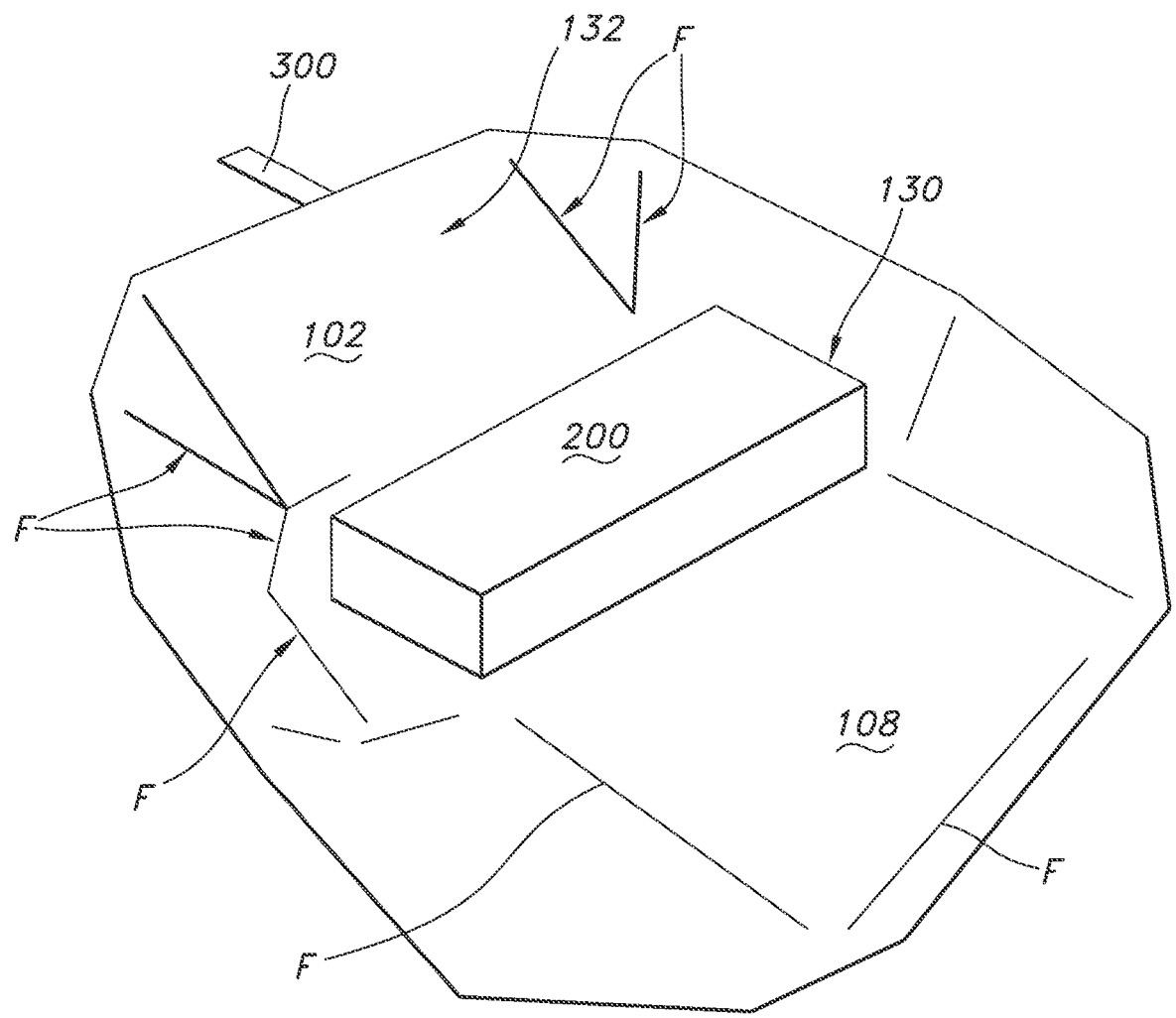
FIG. 8D is in illustration of sterilization assembly during unfolding highlighting imprinted creases, folds and other deformations that prevent portions of the assembly from laying flat during unfolding.
Figure 8E:
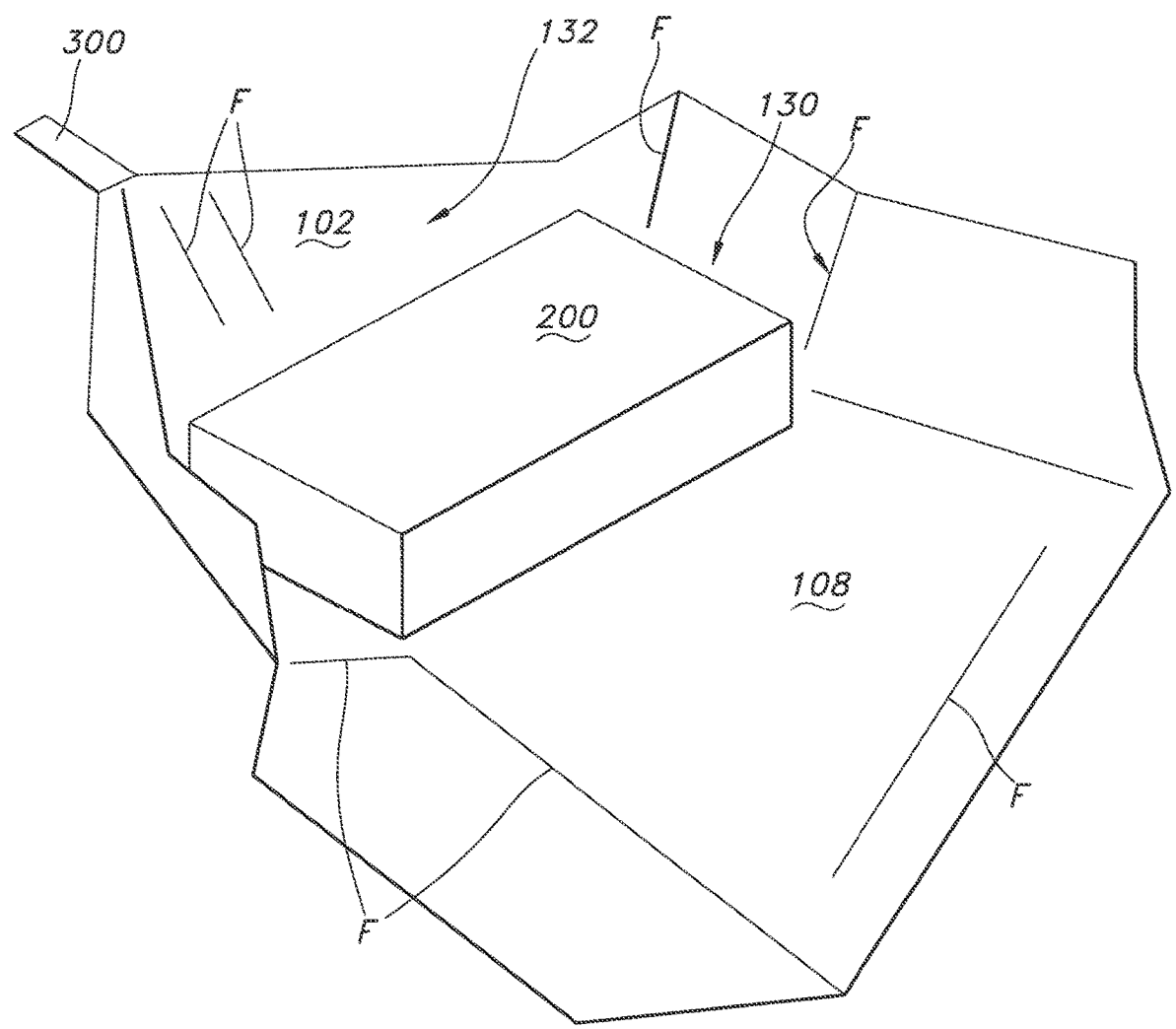
FIG. 8E is in illustration of sterilization assembly during unfolding highlighting imprinted creases, folds and other deformations that cause partially unfolded sides of the assembly to fold back up over the sterilized article or tray while other portions of the assembly are being unfolded.

An important part of the multi-panel sterilization assembly of the present invention are barrier panel bolsters that prevent the barrier panel from folding back on itself, i.e. back towards the unfolded position, during unfolding of the barrier panel, particularly after enhanced steam or heat sterilization. In the absence of these barrier panel bolsters, the side edges of the barrier panel may fold back up onto the sterilized content. Referring now to FIGS. 8D and 8E, when a sterilization wrap or sterilization assembly composed of a material that can set or be "imprinted" under certain conditions such as, for example, nonwoven material made from certain thermoplastic polymers are used in an extended or enhanced steam or heat sterilization process, the nonwoven material may set or "imprint" the shape of the wrapped article or tray (the contents). During unwrapping of the article or tray 200, these imprinted creases, folds or other deformations identified as "F" in FIG. 8D must be overcome during unfolding so the sterilization wrap can lay flat. If the sterilization wrap does not lie flat, it is possible for partially unfolded sides of the sterilization wrap to fold back up over the sterilized article or tray 200 while other portions of the wrap are being unfolded. This phenomenon can compromise the sterility of the article or tray 200. Ordinarily, one would seek to make the material of the sterilization wrap softer, more flexible and compliant so it would fold and unfold more easily and be more able to lay flat during unwrapping/unfolding after sterilization. However, it was unexpectedly discovered that bolstering the sterilization assembly to increase the mass and/or stiffness of the sides significantly reduces or eliminates the likelihood of partially unfolded sides of the sterilization wrap folding back up over the sterilized article or tray while other portions of the wrap are being unfolded.

Referring to FIGS. 6 to 8C, the barrier panel 102 includes barrier panel bolsters 400 located at or adjacent the first edge 120 and the third edge 124 of the barrier panel. These barrier panel bolsters 400 prevent the first and third edges of the barrier panel from folding back on itself, i.e. back towards the unfolded position, during unfolding of the barrier panel, particularly after extended steam or heat sterilization. The barrier panel bolsters 400 can be located at or adjacent the first and third edges (120 and 124, respectively) of the content covering region 132 of the barrier panel 102 and extend inwardly from those edges 120, 124, overlaying the barrier panel 102. Generally speaking, the barrier panel bolsters 400 may be located on the first surface 110 of the barrier panel 102 as illustrated in FIGS. 6, 7A, 7B and 8A. Alternatively and/or additionally, barrier panel bolsters 400 may be located on the second opposing surface 112 of the barrier panel 102 as illustrated in FIG. 7C. The barrier panel bolsters 400 may also be configured to provide reinforcement to the barrier panel 102. In this regard, the barrier panel bolsters 400 may be used in place of reinforcement elements 302 or the or the barrier panel bolsters 400 may be used in combination with reinforcement elements 302 as illustrated in FIGS. 10A to 10D.

The barrier panel bolsters 400 in the content covering region 132 of the barrier panel 102 may also extend into the content receiving region 130 of the barrier panel as illustrated, for example, by FIGS. 6, 7A, 7B and 8A. Alternatively, the barrier panel bolsters 400 may be provided only in the content covering region 132 of the barrier panel 102 as illustrated in FIG. 8C. The barrier panel bolsters may provide reinforcement to the barrier panel in the content receiving portion and also define an area for receiving content to be sterilized.

In an aspect of the invention, the barrier panel bolsters increase the basis weight of the barrier panel by more than about 5 percent at or adjacent the edges of the barrier panel. For example, the barrier panel bolsters may increase the basis weight of the barrier panel by 10 percent to about 75 percent at or adjacent the edges of the barrier panel. As another example, the barrier panel bolsters may increase the basis weight of the barrier panel by 15 percent to about 50 percent at or adjacent the edges of the barrier panel. As yet another example, the barrier panel bolsters may increase the basis weight of the barrier panel by 20 percent to about 40 percent at or adjacent the edges of the barrier panel. As used herein, the term "basis weight" refers to the weight of a material per specified unit of surface area. This measure is usually associated with relatively thin, flat, sheet-like materials such as, for example, fabrics, films, papers, webs and the like. Basis weights of the materials discussed herein were determined essentially in accordance with Method 5041 of Federal Test Method Standard No. 191A. Basis weight may also be measured using test procedure ASTM D 3776-96 or TAPPI Test Method T-220. Basis weight is expressed in units of weight per unit of area (e.g., grams per square meter or ounces per square yard). These units may be abbreviated as "gsm" or "osy", respectively.

In another aspect of the invention, the attachment of the bolsters may stiffen the barrier panel at or adjacent the edges of the barrier panel more than about 5 percent than the stiffness of the overlaid but unattached bolsters and barrier panel. That is, after the barrier panel and the bolsters are joined together by bonding techniques such as, for example, ultrasonic bonding, thermal bonding, bar sealing, adhesive bonding, or the like, the attached layers are more than about 5 percent stiffer than the stiffness of the combined or overlaid but unattached layers that are not joined together. For example, the attachment of the bolsters may stiffen the barrier panel at or adjacent the edges of the barrier panel 10 to about 75 percent more than the stiffness of the combined or overlaid but unattached bolsters and barrier panel. As another example, the attachment of the bolsters may stiffen the barrier panel at or adjacent the edges of the barrier panel 15 to about 50 percent more than the stiffness of the combined or overlaid but unattached bolsters and barrier panel. As yet another example, the attachment of the bolsters may stiffen the barrier panel at or adjacent the edges of the barrier panel 20 to about 40 percent more than the stiffness of the combined or overlaid but unattached bolsters and barrier panel. The stiffness may be characterized as drape stiffness. Drape stiffness may be readily determined using a stiffness tester available from Testing Machines, Amityville, Long Island, N.Y. 11701 and measured in accordance with ASTM standard test D1388-64 using the method described under Option A (Cantilever Test). Alternatively and/or additionally, the stiffness may be characterized as a Kawabata bending stiffness, Gurley stiffness or other measure of stiffness.

The barrier panel bolsters may include one or more layers of materials selected from fibrous webs, impermeable films, permeable or porous films, apertured films, foams and combinations thereof. For example, fibrous webs may include those that are woven and nonwoven. Woven webs may include natural or synthetic materials or blends of the same. As examples, natural materials could be weaves of cotton yarn, and synthetic materials could be weaves of polypropylene, polyester, or nylon yarn and the like. Nonwoven webs may include, for example, spunbond, meltblown, carded webs, wet formed or airlaid webs, or laminates of the same (e.g., spunbond/meltblown/spunbond). Such nonwoven webs may also include natural or synthetic materials or blends of the same. The barrier panel bolsters may include one or more layers of material selected from permeable or impermeable films or laminates of the same. Permeable films may be apertured or be microporous. Apertured films may be obtained through mechanical aperturing, vacuum aperturing, or other commercially available techniques. Microporous films and other similar films may be produced as generally described at, for example, U.S. Pat. Nos. 5,695,868; 5,698,481; 5,855,999; and 6,277,479; the contents of which are incorporated herein by reference. Impermeable films can be monolayer or coextruded and can be comprised of film materials including, for example, polyethylenes, polypropylenes, copolymers thereof, vinyls, metal foils, and the like. It should also be noted said films may also be laminated with fibrous webs, described above.

For example, the barrier panel bolster may be a layer or layers of nonwoven material that is joined to the barrier panel by adhesives, thermal bonding, ultrasonic bonding or other techniques or combinations of techniques. For example, each barrier panel bolster may be a layer of nonwoven material such as, for example, a laminate of two layers of spunbond fabric sandwiching a layer of meltblown fabric (commonly referred to as "SMS" material). Each layer may extend from or adjacent the respective first and third edges of the barrier panel. The barrier panel bolster may extend from at or adjacent the edge to a few inches from the edge or it may extend even further from the edge to help reinforce the barrier panel against tears, punctures, pressure cuts and the like. For example, the barrier panel bolsters extending inwardly from at or adjacent the first and third edges of the barrier panel may each have a width ranging from about 10 percent of the width "W" of the barrier panel up to 40 percent of the width "W" of the barrier panel. Desirably, the barrier panel bolsters extending inwardly from at or adjacent the first and third edges of the barrier panel may each have a width ranging from about 20 percent of the width "W" of the barrier panel up to 40 percent of the width "W" of the barrier panel. Even more desirably, the barrier panel bolsters extending inwardly from at or adjacent the first and third edges of the barrier panel may each have a width ranging from about 30 percent of the width "W" of the barrier panel up to 40 percent of the width "W" of the barrier panel.

Each barrier panel bolster may be joined to the barrier panel over only a portion of its surface that directly contacts the barrier panel. Alternatively, each barrier panel bolster may be joined to the barrier panel over the entire surface of the bolster that directly contacts the barrier panel. For example, the barrier panel bolster may be joined to the barrier panel utilizing a spray of adhesive, a slot-coat application of adhesive, swirl pattern of adhesive over its entire surface—or over only a portion of its surface and particularly to attach the portions of the barrier panel bolster that are inward from the edges of the barrier panel. Attachment of the portions of the barrier panel bolster that are inward from the edges of the barrier panel can be accomplished by applying discrete stripes, lines or swatches of adhesive on the bolster in the direction generally parallel to the first and third edges of the barrier panel. The portions of the barrier panel bolster that are at or immediately adjacent from the edges of the barrier panel may be attached utilizing adhesives as described above or by ultrasonic bonding, thermal bonding, pressure bonding or other techniques. When adhesives are utilized, the adhesive should withstand sterilization conditions. It is also thought that an adhesive which can add to the weight and/or stiffness of the barrier panel bolster would be desirable.

The multi-panel sterilization assembly 100 includes a panel attachment means 106 located on the first surface 110 between the pre-determined fold line 116 and the midpoint "M" of the barrier panel. The panel attachment means 106 is desirably at or near the first edge 120 and/or or the third edge 124 of the barrier panel. Although the panel attachment means 106 is illustrated at or near both the first edge 120 and the third edge 124 of the barrier panel, the panel attachment means 106 may be at or near only one of these edges. As illustrated in FIGS. 6, 7A, 7B, and 8A, the panel attachment means 106 may be located on or joined to the barrier panel bolsters 400.

Figure 7B:
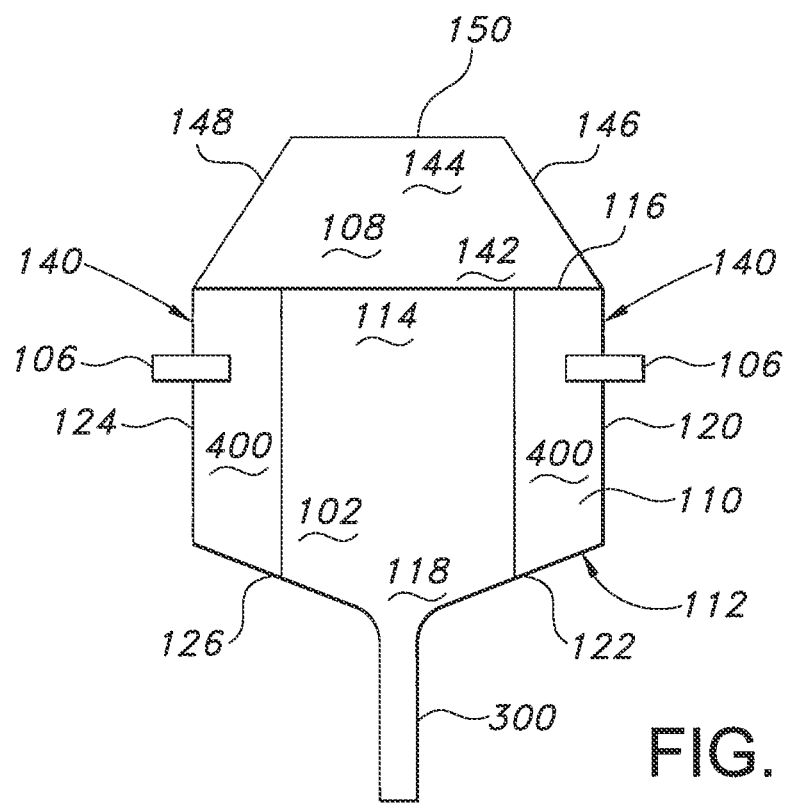
FIG. 7B is an illustration of an exemplary disposable flexible multi-panel sterilization assembly including barrier panel bolsters as well as an integral pull tab.
Figure 9A:
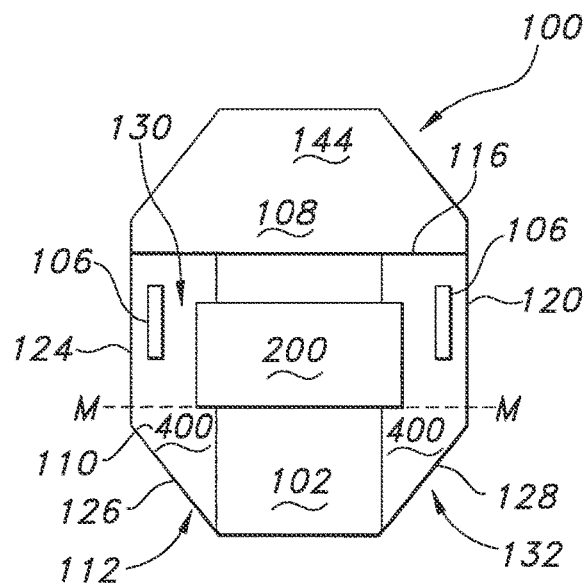
FIGS. 9A to 9E are illustrations of an exemplary sequence of folding an exemplary disposable flexible multi-panel sterilization assembly including barrier panel bolsters.

The panel attachment means 106 may be located at and extend from the first edge 120 and the third edge 124 of the barrier panel as generally illustrated in FIGS. 6 and 7A and 7B. Alternatively and/or additionally, the panel attachment means 106 may be located generally near the first edge and/or the third edge as illustrated in FIG. 8A and FIG. 9A. The panel attachment means may be one large element or a number of discrete elements. Exemplary panel attachment means include, but are not limited to, adhesive tape, double-sided adhesive tape, cleavable release tapes, layered release tapes, cohesive materials, hook and loop fastening systems, mechanical fastening systems including, but not limited to, snaps, clips, magnets, catches, slots and tabs, and combinations thereof. For example, the panel attachment means may be one or more lengths of adhesive tape having at least an end or portion that is stitched, ultrasonically bonded, thermo-mechanically bonded or adhered or adhesively bonded to the barrier panel. Desirably, the panel attachment means is a barrier panel attachment means that is located on the barrier panel and is used to join one or more edges of the barrier panel to itself. It has been found that barrier panel attachment means may be a double sided tape having the same or different levels of adhesive or tack strength of adhesive on each side. Alternatively and/or additionally, the panel attachment means may have a double sided tape structure in which the central layer sandwiched by the adhesive is a splittable or separable material such as a splittable paper, splittable laminate, splittable foam, cleavable paper, cleavable release structure, cleavable foam or other cleavable or separable laminate. Exemplary splittable or cleavable materials are disclosed at, for example, U.S. Pat. No. 5,702,555 issued to Caudal et al. on Dec. 30, 1997; U.S. Pat. No. 4,310,127 issued to Frye on Jan. 12, 1982; U.S. Pat. No. 3,675,844 issued to Sorrell on Jul. 11, 1972; and U.S. Pat. No. 2,205,956 issued to Humphner on Jun. 25, 1940; the contents of which are incorporated by reference.

According to an aspect of the invention, the panel attachment means 106 may be in the form of an adhesive fastening tab or tape closure system such as the various types frequently used on diapers, incontinent garments and similar products. An exemplary tape closure system may be found at, for example, U.S. Pat. No. 4,410,325 issued to Lare on Oct. 18, 1983; the contents of which are incorporated by reference. This system utilizes an adhesive fastening tab or tape closure system (referred to herein as a "tape") that is folded back on itself and which has a first end or portion that is attached to the article (e.g., one part of a garment). During use, the tape is unfolded to reveal an exposed adhesive surface at least at a second end or portion of the tape which is then adhered to a different part of the article (e.g., a second part of the garment) to secure the two parts of the garment in the desired configuration. Generally speaking, the first end of the tape panel attachment means 106 would be secured at or near the first edge 120 of the barrier panel and the second end of the tape panel attachment means 106 would be folded back onto the first end. An additional panel attachment means 106 may be secured at or near the third edge 124 of the barrier panel in a similar manner. During use, the tape panel attachment means 106 would be unfolded to reveal an exposed adhesive surface or surfaces at least at the second end of the panel attachment means 106. The exposed adhesive surface(s) of the panel attachment means at first edge 120 and/or third edge 124 of the barrier panel would be used to secure those portions of the barrier panel to each other and/or to other portions of the barrier panel after the barrier panel is folded about content to be sterilized. In such a configuration, an optional attachment zone 305 may be utilized. An exemplary optional attachment zone 305 is indicated by broken lines in FIG. 8B and in FIG. 9B. In embodiments that utilize adhesive or cohesive materials for the panel attachment means, the attachment zone 305 may be an applied film, a more securely bonded portion of a nonwoven fabric, a separate piece of a material, a coating or the like that provides a suitable surface for the adhesive to bond securely so folded barrier panel does not "pop" open or release when it should not do so. The attachment zone 305 may be configured to signal to a user the appropriate location or locations to secure the panel attachment means. In such configuration, the attachment zone 305 may be combined with or may incorporate indicia such as color, texture, alphanumeric characters or the like to direct a user. More importantly, the attachment zone 305 can be configured to provide a suitable surface such that the force required to release the panel attachment means 106 is carefully controlled to preserve aseptic opening, avoid tearing or shredding of the barrier fabric, provide a satisfactory level of resistance to sheer forces, and/or provide a satisfactory or controlled level of resistance to peel forces.

Another exemplary tape closure system may be found at, for example, U.S. Pat. No. 4,585,450 issued to Rosch et al. on Apr. 29, 1986; the contents of which are incorporated by reference. This system utilizes an adhesive fastening tab or tape closure system (referred to herein as a "tape") that includes a secondary tape element and a primary tape element. The tape has a first end or portion that is attached to the article (e.g., one portion of a garment). The second end or portion contains the secondary tape element and primary tape element. During use, an adhesive surface of the primary tape element is exposed. The adhesive surface of the primary tape element is then adhered to a different part of the article (e.g., a second part of the garment) to secure the two parts of the garment in the desired configuration. An adhesive bond between the primary tape element and the secondary tape element has less strength than the adhesive bond between the primary tape element and the second part of the garment or article such that the bond between the primary tape element and secondary tape element may be reliably separated, repeatedly if necessary.

Generally speaking, the first end or a first side of a panel attachment means 106 would be secured at or near the first edge 120 of the barrier panel and the second end or the second side of the tape panel attachment means 106 would be folded back onto the first end or otherwise covered by a release element. An additional panel attachment means 106 may be secured at or near the third edge 124 of the barrier panel in a similar manner. During use, the primary tape element of the panel attachment means 106 would be unfolded or uncovered to reveal an exposed adhesive surface (s) at least at the second end or second side of the panel attachment means 106. The exposed adhesive surface(s) of the primary tape element of would be used to join the first edge 120 and/or third edge 124 of the barrier panel to each other or to other portions of the barrier panel after the barrier panel is folded about content to be sterilized. In such a configuration, the adhesive bond between the primary tape element and the secondary tape element has less strength than the adhesive bond between the primary tape element and the portion of the barrier panel to which it is adhered such that the bond between the primary tape element and secondary tape element may be reliably separated, repeatedly if necessary. In some respects, the primary tape element may function as an attachment zone. That is, after the primary tape element is adhered to the barrier panel to secure the barrier panel in a folded configuration, the primary tape element may provide a suitable surface such that the force required to overcome the adhesive bond between the primary tape element and the secondary tape element is carefully controlled to preserve aseptic opening, avoid tearing or shredding of the barrier fabric, provide a satisfactory level of resistance to sheer forces, and/or provide a satisfactory or controlled level of resistance to peel forces. In another aspect, the attachment zone 305 as describe previously or in the form of the primary tape element may be used to allow a worker to re-open the wrapped barrier panel prior to inspect contents prior to sterilization and then re-attach the panel attachment means without having to destroy the multi-panel sterilization assembly.

As another example, the panel attachment means may be a length of fabric such as nonwoven fabric having an end or portion that is stitched, ultrasonically bonded, thermo-mechanically bonded or adhered or adhesively bonded to the barrier panel and having a hook fastener from a hook and loop fastening system joined to the other end. It is contemplated that the barrier fabric itself may function as the loop component of a hook and loop fastening system such as hook and loop fastenings systems available as VELCRO® brand fastener products from Velcro Industries B.V. Other exemplary hook systems may be used such as the hook system described in U.S. Pat. No. 5,315,740 issued to Nestegard which relates to hooks having small dimensions so they engage low cost loop materials such as nonwoven webs.

It is contemplated that various elements or components of the panel attachment means, may be integrally formed, such as by molding, co-extrusion or the like, along with any associated substrate layer. For example, the individual hook elements may be integrally formed simultaneously with a hook base-layer by coextruding the base layer and hook elements from substantially the same polymer material.

According to an aspect of the invention, the panel attachment means 106 is joined to the first surface 110 of the barrier panel 102 at a pre-determined position 140 to identify or distinguish the content receiving region 130 of the barrier panel 102 from the content covering region 132 as generally illustrated in FIGS. 6 and 9A. The location of the panel attachment means 106 at the pre-determined position 140 also signals to a user an optimum zone or region within the content receiving region 130 to place content. This may be highlighted by indicia on the assembly and/or instructions on the assembly or which accompany the assembly and which may be posted in the workplace or displayed at a wrapping station.

Referring to FIGS. 8A and 9A, the panel attachment means 106 is desirably a double sided tape having a length that is greater than its width. For example, the panel attachment means may be a double sided tape having a length that more than two times great than its width. As another example, the panel attachment means may be a double sided tape having a length that is four times great than its width to eight times greater than its width. Alternatively and/or additionally, the configuration of the panel attachment means may be a series of tape squares arranged along or near the first edge 120 and the third edge 124. The portion of the panel attachment means 106 closest to the pre-determined fold line 116 is desirably less than about 3 inches from the pre-determined fold line 116. More desirably, the portion of the panel attachment means 106 closest to the pre-determined fold line 116 is desirably less than about 2 inches from the pre-determined fold line 116. For example, the portion of the panel attachment means 106 closest to the pre-determined fold line 116 may be about 1 inch to about ½ inch from the pre-determined fold line 116.

Referring again to FIG. 6, the fold protection panel 108 of the multi-panel sterilization assembly 100 is in juxtaposed communication with the barrier panel 102. That is, the fold protection panel 108 is in side-by-side relationship with or adjoins the barrier panel 102. Generally speaking, the fold protection panel 108 may be any suitable material but desirably is formed of a permeable sheet material. According to the invention, the fold protection panel includes a proximal end 142 generally adjacent the pre-determined fold line 116; a distal end 144 generally opposite the proximal end 142; and at least a first edge 146 and a second edge 148 extending from the proximal end 142 to the distal end 144. According to the present invention, the fold protection panel may have additional edges. For example and with reference to FIG. 7A, the fold protection panel may include at least a third edge 150 located at or along its distal end 144. As yet another example and referring now to FIG. 8A, the fold protection panel may include at least a third edge 150 located at or along its distal end 144 and a fourth edge 152 and a fifth edge 154.

Generally speaking, the fold protection panel may be a lightweight material such as a lightweight laminate of spunbond nonwoven material or a lightweight laminate of spunbond nonwoven material and meltblown nonwoven material. As such, the fold protection panel does not need to provide a higher level of barrier properties like the material that forms the barrier panel. The fold protection panel may be configured so it has barrier properties. For example, the fold protection panel may be formed of the same material as the barrier panel. It is contemplated that the fold protection panel may be a single layer of spunbond nonwoven material.

In an aspect of the invention, the fold protection panel desirably has a width that is the distance from the first edge to the second edge and a length that is the distance from the proximal end to the distal end. The fold protection panel may have a width of from about 12 inches (~30 cm) to about 50 inches (~127 cm). Desirably, the fold protection panel may have a width of from about 18 inches (~46 cm) to about 40 inches (~102 cm). Even more desirably, the fold protection panel may have a width of from about 20 inches (~51 cm) to about 30 inches (~76 cm). The fold protection panel may have a length of from about 6 inches (~15 cm) to about 30 inches (~76 cm). Desirably, the fold protection panel may have a length of from about 8 inches (~20 cm) to about 20 inches (~51 cm). Even more desirably, the fold protection panel may have a length of from about 12 inches (~30 cm) to about 15 inches (~38 cm).

During use, panel attachment means 106 are used to join the barrier panel's first edge 120 and third edge 124 to a portion of the content covering region 132 after the barrier panel 102 has been folded at or near its midpoint "M" such that its second end 118 is brought near its first end 114. It is contemplated that in some embodiments, the panel attachment means 106 may be used to join the barrier panel's first edge 120 and third edge 124 to each other.

According to an aspect of the invention, it is important that the adhesive force or the engagement force at which the panel attachment means join the respective edges of the barrier panel to the content covering region of the barrier panel or to the edges themselves should be sufficient to secure the barrier panel around the content thereby forming a package that is robust and able to withstand normal handling before as well as after sterilization. When the panel attachment means are located on or joined to the barrier panel bolster 400, it is also important that the adhesive force or the engagement force at which the panel attachment means join the respective edges of the barrier panel to the content covering region of the barrier panel or to the edges themselves should be less than the adhesive force or engagement of the barrier panel bolster to the barrier panel, yet sufficient to secure the barrier panel around the content thereby forming a package that is robust and able to withstand normal handling before as well as after sterilization.

In exemplary arrangements, especially where there are sufficiently high levels of engagement shear force provided by the panel attachment means, the fastening engagement may provide a peel force value of not less than a minimum of about 5 grams-force (gmf) (about 0.012 lbs-force) between the panel attachment means and the other portion of the barrier panel that it secures together. In further arrangements, the fastening engagement may provide a peel force value of between about 6 gmf and about 50 gmf to provide improved advantages. In desired configurations, the fastening engagement may provide a peel force value about between about 10 gmf and about 30 gmf between the panel attachment means and the other portion of the barrier panel that it secures together. More desirably, the peel force value may be between about 15 gmf and about 20 gmf. Generally speaking, the peel force should not be more than about 100 gmf, and desirably is not more than about 75 gmf to further provide improved benefits. When the peel force is greater than these values, there is difficulty opening/unwrapping the package containing sterilized contents in an aseptic manner.

The engagement force between the panel attachment means and the other portion of the barrier panel that it secures together may additionally provide a shear force value that is desirably greater than about 5,000 gmf for a panel attachment means having dimensions of about 4 by 1 inches (~102 by ~25 mm). Generally speaking, the resistance to shear force should not be less than about 750 gmf per square inch of the area of engagement between the panel attachment means and the other portion of the barrier panel that it secures together. Desirably, the shear force is not less than about 1,000 gmf/square inch, and more desirably, is not less than about 2,000 gmf/square inch. Even more desirably, the shear force is not less than about 2,500 gmf/square inch. In further aspects, the shear force can be up to about 4,400 gmf/square inch, or more. Alternatively, the shear force is not more than about 3,900 gmf/square inch, and optionally is not more than about 3,500 gmf/square inch to provide improved performance.

The peel force value can be determined utilizing the procedure set forth below in the Examples section. Alternatively, the peel force value can be determined in accordance with standard procedure ASTM D-5170, approved Sep. 15, 1991 and published November 1991.

The shear force value can be determined utilizing the procedure set forth below in the Examples section. Alternatively, the shear force value can be determined in accordance with standard procedure ASTM D-5170, approved Sep. 15, 1991 and published November 1991. The test specimen is composed of the panel attachment means and the portion of the barrier panel to which it secures. The test specimen length and width typically correspond to the length and width employed to conduct the subsequently described testing for peel force value. During testing, the test specimen length is aligned perpendicular to the direction in which a shear force is typically applied to the panel attachment means (e.g., double sided tape fastener) during the ordinary use of the article with which the fastener is employed. The specimen "width" is perpendicular to the specimen length. That is, shear force is typically applied across the width of the specimen (i.e., perpendicular to the length) for a specimen having a length that is greater than its width—which is the configuration illustrated in FIGS. 8A and 9A.

It should be readily appreciated that the adhesive force or the engagement force at which the panel attachment means join the respective edges of the barrier panel to the content covering region of the barrier panel or to the edges themselves should be less than the peel strength of the bond that is used to join the panel attachment means to the underlying barrier panel or component such as the barrier panel bolster during construction of the assembly. For example, the peel strength of the bond (e.g., adhesive, mechanical, thermomechanical, ultrasonic, etc.) that is used to join the panel attachment means to the underlying barrier panel during construction should be much greater than about 400 gmf for a panel attachment means having a dimension of about 4 inches by 1 inch (about 10 cm by 2.5 cm). Desirably, the peel strength of the bond that is used to join the panel attachment means to the underlying barrier panel during construction should be greater than about 400 gmf per square inch of the area of engagement between the panel attachment means and the barrier. For example, the bond strength may be more than 1000 gmf/square inch, and may be more than 4,000 gmf/square inch. When the panel attachment means are located on or joined to the barrier panel bolster 400, it is important that the adhesive force or the engagement force at which the panel attachment means join the respective edges of the barrier panel to the content covering region of the barrier panel or to the edges themselves should be less than the strength of the bond between the barrier panel bolster and the barrier panel.

Referring now to FIGS. 9A through 9E (and with additional reference to FIG. 8A), there is illustrated an example of a multi-panel sterilization assembly in an exemplary sequence of folding. FIG. 9A illustrates a multi-panel sterilization assembly 100 composed of barrier panel 102 which cooperates with the fold protection panel 108 and the panel attachment means 106 on the first surface 110 so the barrier panel 102 can be folded around the content 200 to form a package (such as the package 202 generally illustrated in FIG. 9E). The barrier panel 102 is the portion of the flexible multi-panel sterilization assembly 100 that contacts and covers the content 200. The content 200 is placed in the content receiving 130 which is generally defined by the panel attachment means 106 on the first surface 110 of the barrier panel 102.

Figure 9B:
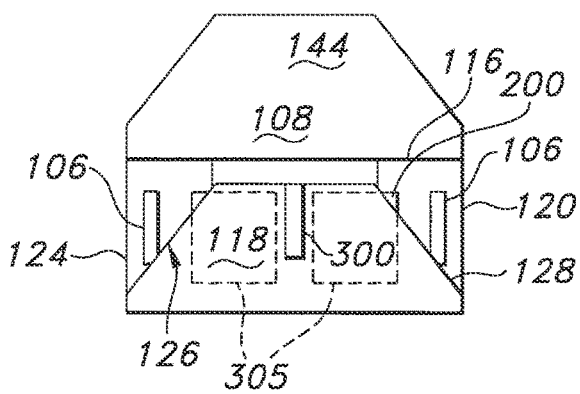

As generally illustrated in FIG. 9B, the second end 118 of the barrier panel 102 is folded up at the midpoint "M" and brought to the first end 114 so the content covering region 132 of the barrier panel 102 extends over the content 200. As shown in FIG. 9B, the width of the barrier panel at the second end 118 is less than the width of the barrier panel at the first end 114. This is important when the panel attachment means 106 are located directly on the barrier panel as shown in FIGS. 8A and 9A (rather than extending outward from the edges as illustrated in FIGS. 7A and 7B) because it provides a configuration of the fourth edge 126 and the fifth edge 128 that allows access to the panel attachment means 106 after the second end 118 is brought up to the first end 114.

Figure 7C:
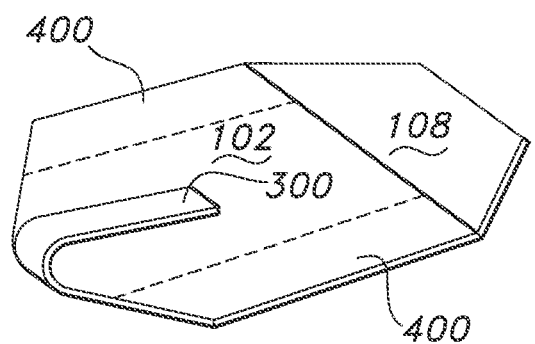
FIG. 7C is an illustration highlighting a detail of the exemplary disposable flexible multi-panel sterilization assembly of FIG. 7B and illustrating optional barrier panel bolsters.

In some embodiments of the present invention, a pull tab or tail 300 is extends from the second end 118 so that the pull tab or tail 300 is positioned to be accessible during the initial steps of unfolding or unwrapping a wrapped package. The pull tab or tail 300 desirably extends from or is joined to the second end 118 of the barrier panel on the second opposing surface 112 of the barrier panel 102. Referring briefly to FIG. 7B, there is shown a configuration in which the pull tab or tail 300 is unitary or integral with the barrier panel. FIG. 7C illustrates that pull tab or tail 300 on the second opposing surface 112 of the barrier panel 102. The distal end (i.e., the loose end) of the pull tab or tail 300 is desirably secured to the barrier panel with a light adhesive or an adhesive tab or sticker such that the pull tab or tail 300 does not flop around during wrapping and is in an appropriate position during unwrapping.

Figure 9C:
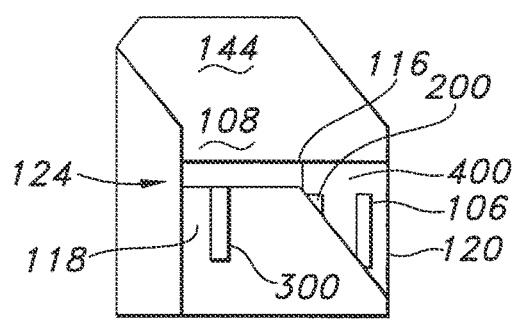

Referring now to FIG. 9C, that illustration shows that the third edge 124 of the barrier panel 102 is folded over the second end 118 (after the second end 118 is brought up to the first end 114). While not necessarily shown to scale, the third edge 124 of the barrier panel 102 after folding does not extend very far toward the middle of the assembly.

Figure 9D:
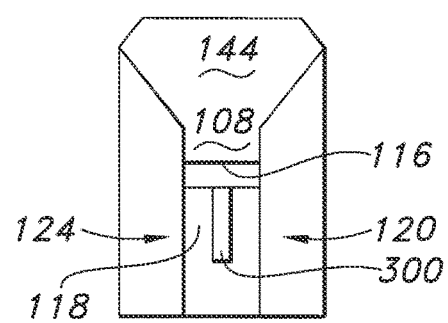

FIG. 9D illustrates that the first edge 120 of the barrier panel 102 is folded over the second end 118. While not necessarily shown to scale, the first edge 120 of the barrier panel 102 upon folding does not extend very far toward the middle of the assembly. Accordingly, it is evident that the third edge 124 and the first edge 120 generally do not overlap. Unlike conventional sterilization wrap in which the edges are intentionally overlapped as generally illustrated in FIGS. 4 and 5, the edges 120 and 124 of the barrier panel are separated by a distance. This difference highlights the importance of the panel attachment means 106 to hold the folded edges 120 and 124 of the barrier panel 102 in place about the content. Moreover, having these edges generally exposed highlights the importance of the fold protection panel 108.

Figure 9E:
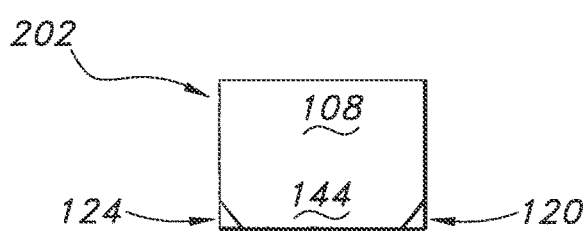

Referring now to FIG. 9E, the fold protection panel 108 is folded at the pre-determined fold line 116 bringing its distal end 144 over the second end 118 of the barrier panel. In some embodiments, a portion of the material adjacent the first edge 120 and the third edge 124 may be visible. With this configuration, the actual edges 120 and 124 of the barrier panel 102 are fully covered so the edges themselves are less susceptible to being accidentally pulled open or breached during normal handling of the package. The fold protection panel is typically secured utilizing conventional tape that is used with sterilization wrap. Desirably, the fold protection panel covers the edges of the barrier protection panel after it is folded around the content to be sterilized to form a package. The fold protection panel covers these edges to prevent a worker inadvertently opening the folded barrier protection panel. In addition, the fold protection panel shields the edges from snags, pulls or other phenomenon that could impart a peel force to these edges that would cause the panel attachment means to detach. That is, the configuration of the multi-panel sterilization assembly utilizes the fold protection panel to protect exposed edges of the barrier panel after the barrier panel has been folded around content to be sterilized to form a package.

The sequence of unfolding the multi-panel sterilization assembly after it has wrapped around a tray or article and sterilized is generally the reverse of the folding sequence. For example, the conventional tape securing the fold protection panel is broken and the fold protection panel is pulled back to expose the pull tab 300 and portions of the first edge 120 and the third edge 124 to a configuration as generally illustrated by FIG. 9D. The first edge 120 is grasped and pulled up or to the side to detach the panel attachment means and then unfolded flat to a configuration as generally illustrated by FIG. 9C. The third edge 124 is grasped and pulled up or to the side to detach the panel attachment means and the third edge 124 is unfolded flat to the configuration as generally illustrated by FIG. 9B. The pull tab 300 is grasped at the location where it is secured to the barrier panel with an adhesive tab or sticker and the tab or sticker is pulled up and the pull tab 300 and the second end 118 of the barrier panel is pulled away from the content 200. Importantly, the barrier panel bolsters 400 help the first edge 120 and the third edge 124 of the barrier panel remain in a generally flat, unfolded configuration which keeps them from folding back up over the content 200.

According to the present invention, the barrier panel may be composed of at least one layer of a breathable nonwoven material. Desirably, the breathable nonwoven material is a laminate composed of a layer of spunbonded filaments, a layer of meltblown fibers, and a layer of spunbonded filaments—also called spunbonded-meltblown-spunbonded material. The method of making these layers is known and described in commonly assigned U.S. Pat. No. 4,041,203 to Brock et al which is incorporated herein in its entirety by reference. The material of Brock et al is a three layer laminate of spunbonded-meltblown-spunbonded layers which is also commonly referred to by the acronym "SMS". The two outer layers of SMS are a spunbonded material made from extruded polyolefin fibers, or filaments, laid down in a random pattern and then bonded to one another. The inner layer is a meltblown layer also made from extruded polyolefin fibers generally of a smaller diameter than the fibers in the spunbonded layers. As a result, the meltblown layer provides increased barrier properties due to it fine fiber structure which permits the sterilizing agent to pass through the fabric while preventing passage of bacteria and other contaminants. Conversely, the two outer spunbonded layers provide a greater portion of the strength factor in the overall laminate. The laminate may be prepared using an intermittent bond pattern that is preferably employed with the pattern being substantially regularly repeating over the surface of the laminate. The pattern is selected such that the bonds may occupy about 5-50% of the surface area of the laminate. Desirably, the bonds may occupy about 10-30% of the surface area of the laminate. Other combinations and variations of these materials are contemplated. As a non-limiting example, the inner layer may contain two meltblown layers such that the material may be called "SMMS".

When the barrier panel is composed of or incorporates SMS material(s), the basis weight of the SMS material(s) may be from 1 ounce per square yard or "osy" which is approximately (33 grams per square meter or "gsm") to about 3 osy (100 gsm). For example, the basis weight of the SMS material(s) may be from 1.2 osy (40 gsm) to about 2 osy (67 gsm). As another example, the basis weight of the SMS material(s) may be from 1.4 osy (47 gsm) to about 1.8 osy (60 gsm). The basis weight may be determined in accordance with ASTM D3776-07. Multiple plies or layers of SMS material may be used to provide basis weights ranging from about 2 osy (67 gsm) to about 5 osy (167 gsm).

The permeability of the barrier panel may range from 25 to about 500 cubic feet per minute (CFM) as characterized in terms of Frazier permeability. For example, the permeability of the barrier panel may range from 50 to about 400 cubic feet per minute. As yet another example, the permeability of the barrier panel may range from 100 to about 300 cubic feet per minute. The Frazier permeability, which expresses the permeability of a material in terms of cubic feet per minute of air through a square foot of area of a surface of the material at a pressure drop of 0.5 inch of water (or 125 Pa), was determined utilizing a Frazier Air Permeability Tester available from the Frazier Precision Instrument Company and measured in accordance with Federal Test Method 5450, Standard No. 191A. When the barrier panel is composed of or incorporates SMS material(s) have basis weights ranging from about 1 osy (33 gsm) to about 2.6 osy (87 gsm), the permeability of the barrier panel may range from about 20 cubic feet per minute to about 75 cubic feet per minute when determined generally in accordance with ISO 9237:1995 (measured with an automated air permeability machine using a 38 $cm^2$ head at a test pressure of 125 Pa—exemplary air permeability machine is TEXTEST FX 3300 available from TEXTEST AG, Switzerland). If multiple plies or layers of SMS material are used to provide basis weights ranging from about 2 osy (67 gsm) to about 5 osy (167 gsm), the permeability of the barrier panel may range from about 10 cubic feet per minute to about 30 cubic feet per minute when determined generally in accordance with ISO 9237:1995.

As noted above, the flexible multi-panel sterilization assembly 100 may include at least one pull tab 300 extending from the second end 118 of the barrier panel 102. The pull tab 300 may be formed of the same material as the barrier panel or may be formed of one or more different materials. The pull tab is a feature that can be grasped by a person unfolding a sterilized package formed of a folded flexible multi-panel sterilization assembly containing sterilized content without compromising the sterile field formed by the unfolded content-contacting portions of the barrier panel. The pull tab 300 may be attached to the barrier panel or it may be integral or unitary with the barrier panel. In an aspect of the invention, the barrier panel at or adjacent the edges near the pull tab 300 may be bonded together utilizing a seam such as, for example, a stitched seam, an ultrasonic bond seam, adhesive bond seam, thermo-mechanical bond seam (e.g., a bar seal seam) or combinations thereof to provide sufficient stiffness, rigidity or support to that portion of the barrier panel so that folding or creasing of the barrier panel is reduced or eliminated when force is applied to the pull tab 300 during unwrapping. This is important to preserve the sterility of the contents during unwrapping. For example, the second edge 122 and the fourth edge 126 illustrated in FIG. 7B may be partially or substantially bonded to provide such a configuration. As another example, the second edge 122 illustrated in FIG. 8A may be partially or substantially bonded to provide the desired configuration. As yet another example, the second edge 122 and/or the fourth edge 126 and fifth edge 128 illustrated in FIG. 8A may be partially or substantially bonded to provide the desired configuration.

In an embodiment of the invention, the sterilization assembly may further include one or more discrete reinforcement elements in the content receiving region. In addition to reinforcing the barrier panel, the reinforcement element may define an area for receiving content to be sterilized. As noted above, the barrier panel bolster may extend into the content receiving region to reinforce the barrier panel and/or define an area for receiving content to be sterilized. Accordingly, the following discussion can be applied to the barrier panel bolster if it is desired for that component to also serve as a reinforcement element in addition to preventing the edges of the barrier panel from folding back on itself during unfolding of the barrier panel. The reinforcement elements may include one or more layers of materials selected from fibrous webs, impermeable films, permeable or porous films, apertured films, foams and combinations thereof. For example, fibrous webs may include those that are woven and nonwoven. Woven webs may include natural or synthetic materials or blends of the same. As examples, natural materials could be weaves of cotton yarn, and synthetic materials could be weaves of polypropylene, polyester, or nylon yarn and the like. Non-woven webs may include, for example, spunbond, melt-blown, carded webs, wet formed or airlaid webs, or laminates of the same (e.g., spunbond/meltblown/spunbond). Such nonwoven webs may also include natural or synthetic materials or blends of the same. The reinforcement elements include one or more layers of material selected from permeable or impermeable films or laminates of the same. Permeable films may be apertured or be microporous. Apertured films may be obtained through mechanical aperturing, vacuum aperturing, or other commercially available techniques.

Reinforcement elements can be discrete zones of the barrier panel containing additional material or treatments to reduce the likelihood that the barrier panel will be compromised by pressure cuts, pressure holes, tears or the like in the locations where the content is likely to concentrate forces against the material(s) of the barrier panel. It is envisioned that relative to the material(s) of the barrier panel, the reinforcement elements can be less permeable or even impermeable to hot air, steam, or other sterilization gas, while still allowing for proper sterilization and removal of sterilant gas. It has been found that acceptable sterilization and removal of sterilant gas will take place if the permeability of the sterilization package web is greater than about 25 cubic feet per minute (cfm) as characterized in terms of Frazier permeability. As such, a reinforcement element material that is impermeable or less permeable than the sterilization package material is acceptable, as long as the overall sterilization package is adequately permeable (i.e., greater than about 25 cfm). If an impermeable or less permeable reinforcement element material is desirable, the permeability of the overall sterilization package can be varied by changing the area covered by the reinforcement element. It is desirable that the sterilization package web maintain an overall permeability of at least about 25 cfm.

The reinforcement elements may also be configured to identify the content receiving region 130 of the barrier panel 102. Alternatively and/or additionally the reinforcement elements may be configured to cooperate with the panel attachment means to identify the content receiving region 130 of the barrier panel 102. For example, the reinforcement elements may be in the form of discrete shapes placed within the content receiving region. FIGS. 10A through 10D are illustrations of exemplary flexible multi-panel sterilization assemblies 100 composed of a barrier panel 102, panel attachment means 106 and a fold protection panel 108 and which further include reinforcement elements 302.

Figure 10A:
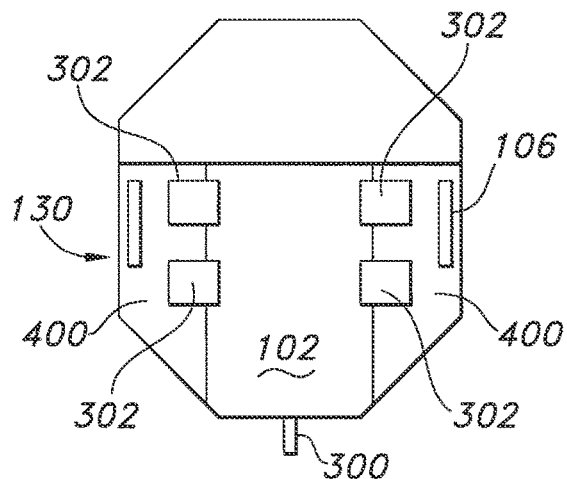
FIGS. 10A to 10D are illustrations of exemplary disposable flexible multi-panel sterilization assemblies showing exemplary barrier panel bolsters and reinforcing elements.
Figure 10B:
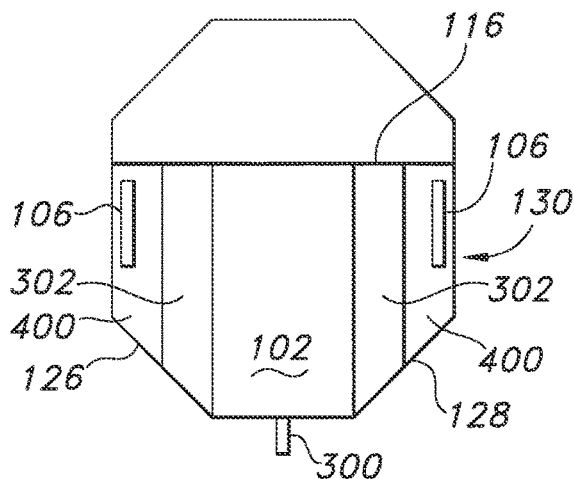
Figure 10C:
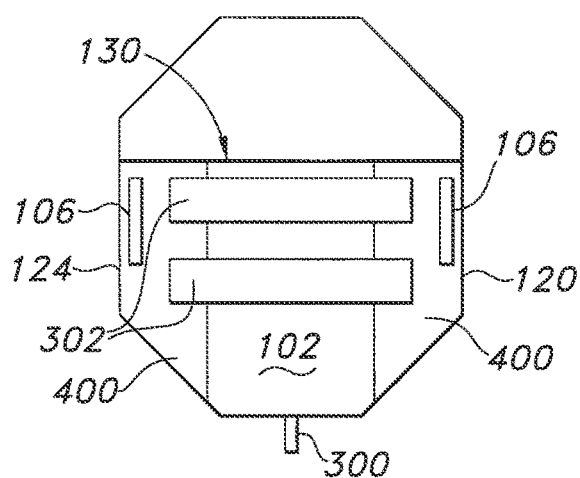
Figure 10D:
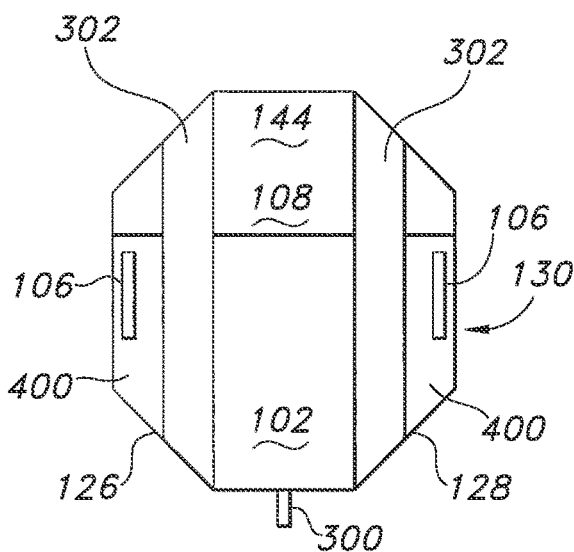

FIG. 10A illustrates a flexible multi-panel sterilization assembly 100 in which four reinforcement elements 302 are positioned at spaced apart locations in the content receiving region 130 of the barrier panel 102 generally at the locations that correspond to the corners of a sterilization tray or similar content. FIG. 10B illustrates a flexible multi-panel sterilization assembly 100 in which two reinforcement elements 302 are positioned at spaced apart locations on the barrier panel 102 extending from the pre-determined fold line 116 to a fourth edge 126 and a fifth edge 128 of the barrier panel 102 generally opposite the pre-determined fold line 116. The two reinforcement elements 302 are positioned in the content receiving region 130 generally at the locations that correspond to the corners of a sterilization tray or similar content. FIG. 10C illustrates a flexible multi-panel sterilization assembly 100 in which two reinforcement elements 302 are positioned at spaced apart locations on the barrier panel 102 generally parallel to the pre-determined fold line 116 between the two panel attachment means 106 at or adjacent a first edge 120 and a third edge 124. The two reinforcement elements 302 are positioned in the content receiving region 130 generally at the locations that correspond to the corners of a sterilization tray or similar content. FIG. 10D illustrates a flexible multi-panel sterilization assembly 100 in which two reinforcement elements 302 are positioned at spaced apart locations on the barrier panel 102 and the fold protection panel 108. The two reinforcement elements 302 extend in generally parallel configuration from a distal end 144 of the fold protection panel 108 to a fourth edge 126 and a fifth edge 128 of the barrier panel 102. The two reinforcement elements 302 are positioned in the content receiving region 130 generally at the locations that correspond to the corners of a sterilization tray or similar content. It should be noted that a pull tab or tail 300 is illustrated in FIGS. 10A to 10D as extending out from underneath the barrier panel. This representation is merely intended to illustrate that a pull tab or tail 300 may be included and not particularly how it is preferably configured.

Figure 11A:
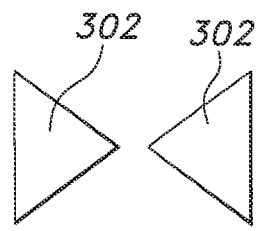
FIGS. 11A to 11B are illustrations of exemplary reinforcing elements.
Figure 11B:
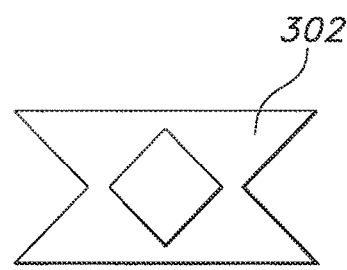

Of course, the reinforcement elements may have a wide variety of shapes, sizes and other configurations. FIGS. 11A and 11B are illustrations of exemplary reinforcement elements 302. FIG. 11A illustrates reinforcement elements 302 having generally triangular configurations. FIG. 11B illustrates an exemplary reinforcement element 302 composed of several overlapping triangular elements. Alternatively and/or additionally, the reinforcement element 302 illustrated in FIG. 11B may be formed by a single piece of material. Other shapes and configurations are contemplated such, for example, "H" patterns, "X" patterns, or the like.

Figure 12:
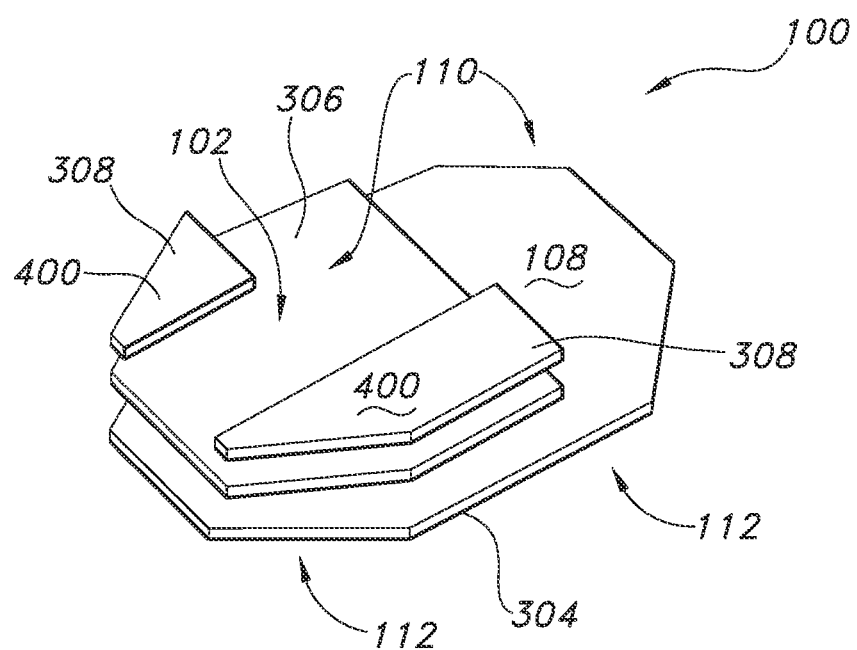
FIG. 12 is an illustration of an exploded or broken apart perspective view of exemplary features of an exemplary disposable flexible multi-panel sterilization assembly including barrier panel bolsters.

In an aspect of the invention, the construction of the disposable flexible multi-panel sterilization assembly may be based on a two primary pieces of material. Referring now to FIG. 12, there is shown an illustration of an exemplary disposable flexible multi-panel sterilization assembly 100 in exploded or broken apart view revealing a first layer 304 of a material, a second layer 306 of material and a third layer of material 308. In this configuration, the first layer 304 of material and the second layer 306 of material overlap to define the barrier panel 102. Generally speaking, these layers may be joined by adhesives, ultrasonic bonding, thermo-mechanical bonding or the like. The layers are desirably joined at or adjacent at least two of the edges and along the pre-determined fold line. For example, the layers may be joined along the first edge 120 and the third edge 124. The bonding may be a complete seam or the edge may be partially bonded along only one or a few portions of the edge. Alternatively and/or additionally, the bonding may be intermittent or discontinuous along all or a portion of the respective edge. Of course, other edges may also be bonded or the layers may be bonded together across all or portions of their entire surface area. The region where there is no overlap of the first layer 304 of material and second layer 306 of material forms the fold protection panel 108. Generally speaking, the first layer 304 of material and the second layer 306 of material may be the same material or they may be different materials. For example, the first layer 304 of material may be single layer or multiple layers of spunbond nonwoven material, a lightweight nonwoven laminate material, or a material that lacks the level of barrier properties (or other characteristics) that may be desired for the barrier panel. The second layer 306 of material desirably has a higher level of barrier properties than the first layer 304 of material. For example, the second layer 306 of material may be a laminate of nonwoven fabrics such as "SMS" material. The third layer of material 308 is the barrier panel bolster 400. Two different barrier panel bolsters are illustrated in FIG. 12. One barrier panel bolster is illustrated as extending the length of the second layer of material 306 which would correspond to a barrier panel bolster that spans both the content covering region of the barrier panel and the content receiving region of the barrier panel. The other barrier panel bolster 400 is illustrated as extending only a portion of the length of the second layer of material 306 which generally corresponds to a barrier panel bolster that spans only the content covering region of the barrier panel.

As generally shown in FIG. 12, the first surface 110 of the disposable flexible multi-panel sterilization assembly 100 may be formed of the third layer of material 308, the second layer 306 of material and the first layer 304 of material and the second opposing surface 112 may be formed of the first layer 304 of material. It is contemplated that the first surface 110 of the disposable flexible multi-panel sterilization assembly 100 may be formed of the first layer 304 of material and the second opposing surface 112 may be formed of the first layer 304 of material, the second layer 306 of material and the third layer of material 308. It is also contemplated that other combinations of layers may be used such that two layers of material generally corresponding in size to the first layer of material 304 may sandwich or enclose an intermediate layer of material corresponding in size to the second layer of material 306 and/or the third layer of material 308 such that the first surface 110 and the second opposing surface 112 are generally the same such that one surface does not reveal other discrete layers of material (i.e., does not show both the first layer 304 of material, the second layer 306 of material and the third layer of material 308). Alternatively, the third layer of material 308 may be sandwiched between the first layer 304 and the second layer 306.

Figure 13:
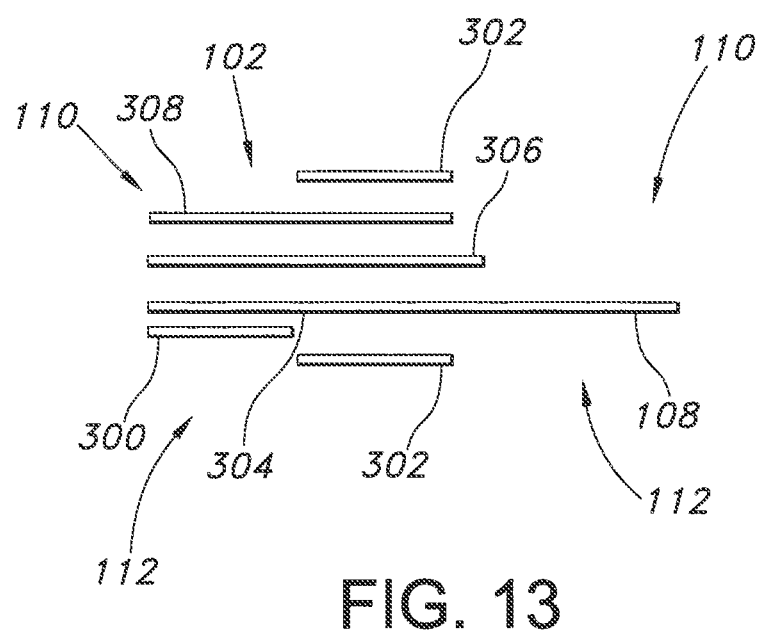
FIG. 13 is an illustration of an exploded or broken apart cross-section view of exemplary features of an exemplary disposable flexible multi-panel sterilization assembly including barrier panel bolsters.

Referring now to FIG. 13, there is shown an illustration of an exemplary disposable flexible multi-panel sterilization assembly 100 in exploded or broken apart cross-sectional view revealing a first layer 304 of a material, a second layer 306 of material and a third layer of material 308. In this configuration, the first layer 304 of material and the second layer 306 of material overlap to define the barrier panel 102. The region where there is no overlap of the first layer 304 of material and second layer 306 of material forms the fold protection panel 108. The portions where the third layer of material overlaps the first layer 304 and the second layer 306 generally forms the barrier panel bolster. The cross-sectional view illustrates reinforcement elements 302 which may be located directly on the third layer 308 of material. The reinforcement elements 302 may be present on the first surface 110 to desirably identify the content receiving region 130 of the barrier panel 102 between the panel attachment means 106. Alternatively and/or additionally, the reinforcement elements 302 may be located on the second opposing surface 112 of the barrier panel.

Sterilization wrap has many modes of failure involving tears, cuts, punctures, holes or other breaches. Any failures may have serious consequences. The more common modes of failure are conventionally believed to involve tears, holes or cuts initiating from the sterilization tray or other content that is wrapped by or otherwise enclosed by conventional sterilization wrap fabric. In other words, tears, cuts or holds were believed to begin at the interface between the sterilization tray or other content and the sterilization wrap fabric itself and propagate from the inside of the sterilization wrap fabric penetrating outwardly through the material ultimately creating a breach. Accordingly, much effort has been expended to develop corner guards and other types of protection that is placed between the sterilization tray or other content and the sterilization wrap.

In an aspect of the present invention, it has been discovered that pressure holes and pressure cuts of the type in which the fibers adjacent the hole or cut appear to have been fused or "welded" together most commonly propagate from the outside of a package (i.e., content enclosed by sterilization wrap fabric) rather than propagating the sterilization tray or other content that is wrapped by or otherwise enclosed by conventional sterilization wrap fabric. Accordingly, the applicants have discovered that locating the reinforcement elements 302 (or the barrier panel bolsters 400 if it is desired for that component to also serve as a reinforcement element in addition to preventing the edges of the barrier panel from folding back on itself during unfolding of the barrier panel) on the second opposing surface 112 of the barrier panel provides an unexpected advantage because the second opposing surface 112 of the barrier panel 102 is the portion of the disposable flexible multi-panel sterilization assembly 100 that does not contact the content (e.g., sterilization tray) and which typically forms the outside of a wrapped package. Reinforcement elements 302 located on the second opposing surface 112 provide more efficient protection against pressure holes and pressure cuts because the inventors have discovered that pressure holds and pressure cuts tend to propagate from the outside of a wrapped package. While the inventors should not be held to any particular theory of operation, it has been discovered that pressure cuts and pressure holes are more frequently caused when content enclosed by sterilization wrap contacts an irregular surface with sufficient force during a single contact event or during multiple contact events such that the irregular surface concentrates the force to generate energy that causes failure.

Such contact events are frequently encountered when an individual wrapped sterilization tray or stacks of wrapped sterilization trays (particularly at overloaded weights) are transported by cart or other similar device and the cart or similar device stops abruptly (e.g., due to impact), encounters bumps or abrupt shocks. Other sources of contact events occur when wrapped trays are dropped (especially on the edge of a cart); when wrapped trays are dragged or pushed across a smooth surface; when a wrapped tray contacts a hard surfaces; and/or when excessive pressure is applied to a wrapped tray. For example, lifting the front end of a 20 pound tray so that all the weight of the tray is resting on the back end, and pulling it across the storage shelf before lifting may produce pressure cuts. As another example, dropping a wrapped tray (even a small distance) onto an edge of a cart or storage shelf while being transported to different areas of the hospital may produce pressure holes.

Generally speaking, the utilization of reinforcement elements reduces pressure hole formation for each of the barrier materials tested. Quantitatively, pressure hole formation is reduced between ~30% and 46%, depending upon what barrier material is tested and the basis weights of the barrier material and the reinforcement elements (corner guards).

When using reinforcement elements in conjunction with a relatively low basis weight barrier material (e.g., about 1 osy), low basis weight reinforcement elements (e.g., from about 0.1 to about 1 osy) result in substantial reduction in pressure hole formation in the barrier material. Further increasing reinforcement element basis weight (e.g., to a basis weight of from about 1 to about 2 osy) results in additional, but more modest, reduction in pressure hole formation in the barrier material. Further increasing the reinforcement element basis weight (e.g., to a basis weight of greater than about 2 osy) appears to provide little, if any, additional improvement in reducing pressure hole formation in the barrier material.

While the inventors should not be held to a particular theory of operation, a relatively "weak" barrier material (e.g., relatively low basis weight) which is not protected by a reinforcing element on the exterior of the barrier material (i.e., the outermost surface of the barrier material) will eventually fail at the same rate regardless of how "strong" (e.g., relatively high basis weight) the reinforcement elements are that might be used on an interior surface (i.e., the interior surface contacting the content to be sterilized or the sterilized content) of the barrier material.

When using reinforcement elements in conjunction with a moderate basis weight barrier material (e.g., basis weight about 1.8 osy), the use of low basis weight reinforcement elements (e.g., basis weights from about 0.1 to about 1 osy) on the interior surface of the barrier material (i.e., the interior surface contacting the content to be sterilized or the sterilized content) results in substantial reduction in pressure hole formation in the barrier material. A similar "plateau", where further increasing the basis weight of the reinforcement element on the interior surface no longer provides additional benefit to the barrier material is believed to exist.

Use of a relatively light weight reinforcement element (~1 osy) reduces pressure hole formation in all basis weights of barrier materials (barrier materials ranging from 1 osy to 2 osy). As the basis weight of the barrier material is increased, basis weight of the barrier material itself becomes the most predominant factor for reinforcement and reduced pressure hole formation. But light weight reinforcement elements still reduce pressure hole formation in the heaviest barrier materials tested (~2 osy), as compared to when reinforcement elements are not used. Extrapolation would suggest that a barrier material of 3 osy or greater would not benefit from a 1 osy reinforcement element.

Generally speaking, the results of this testing show that Percent Failure decreases as the basis weight of the barrier material is increased. However, when reinforcing elements are positioned between the sterilization tray and the barrier material, an increase in the basis weight of the combined components (i.e., the barrier material basis weight is constant and reinforcing element basis weight increases) results in a decrease in Percent Failure that levels off at a much higher rate of failure than for a barrier material having a corresponding basis weight.

Surprisingly, when reinforcing elements are positioned on the outside of the barrier material such that the reinforcing elements come between the barrier material and the surface of a shelf (at least at the corners of the sterilization tray), an increase in the basis weight of the combined components (i.e., the barrier material basis weight is constant and reinforcing element basis weight increases) results in a decrease in failure rates that compares favorably to a barrier material having a corresponding basis weight.

This is interpreted as providing a sterilization assembly in which the basis weight of the barrier panel may be reduced or at least held to a low level while generating a profile of resistance to pressure cuts and pressure holes that was previously provided only by increasing the basis weight of the entire sterilization wrap material.

EXAMPLES

Aspects of the disposable flexible multi-panel sterilization assembly were evaluated in the following examples.

Example 1

Figure 14:
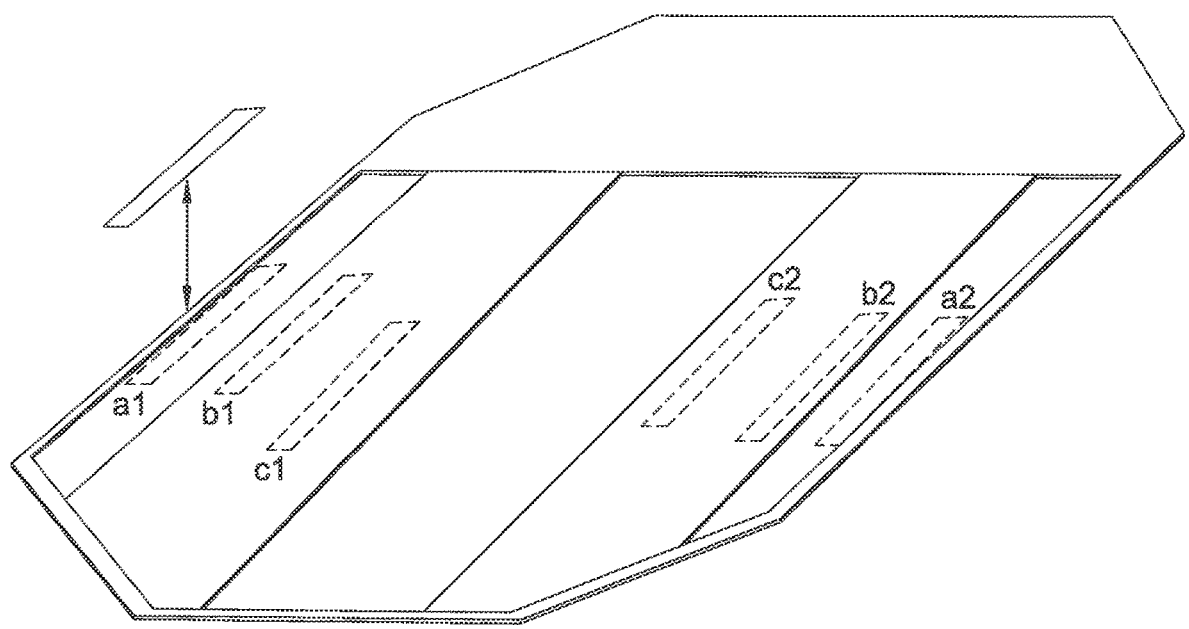
FIG. 14 is an illustration of a perspective view of an exemplary disposable flexible multi-panel sterilization assembly without barrier panel bolsters.
Figure 15:
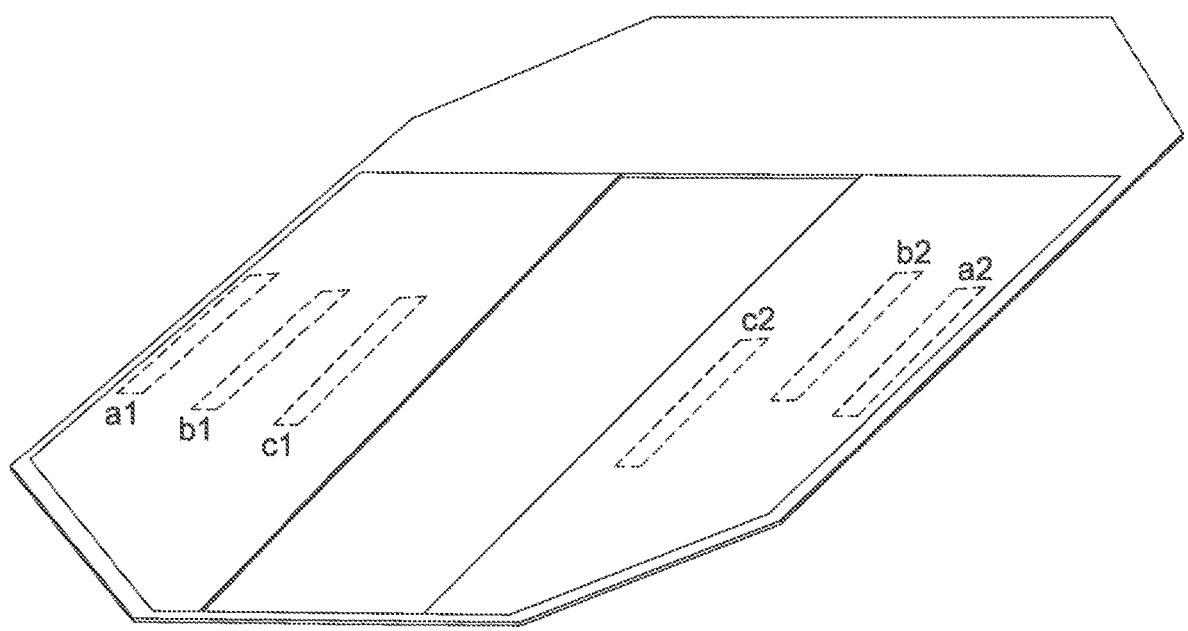
FIG. 15 is an illustration of a perspective view of an exemplary disposable flexible multi-panel sterilization assembly with barrier panel bolsters.
Figure 16:
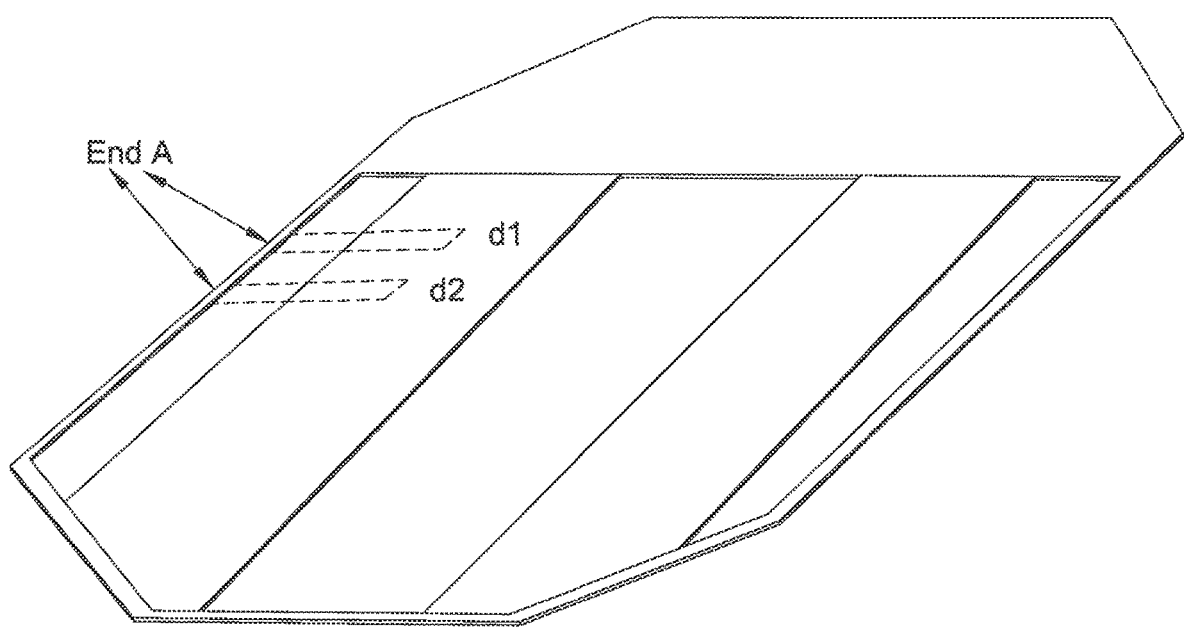
FIG. 16 is an illustration of a perspective view of an exemplary disposable flexible multi-panel sterilization assembly without barrier panel bolsters.
Figure 17:
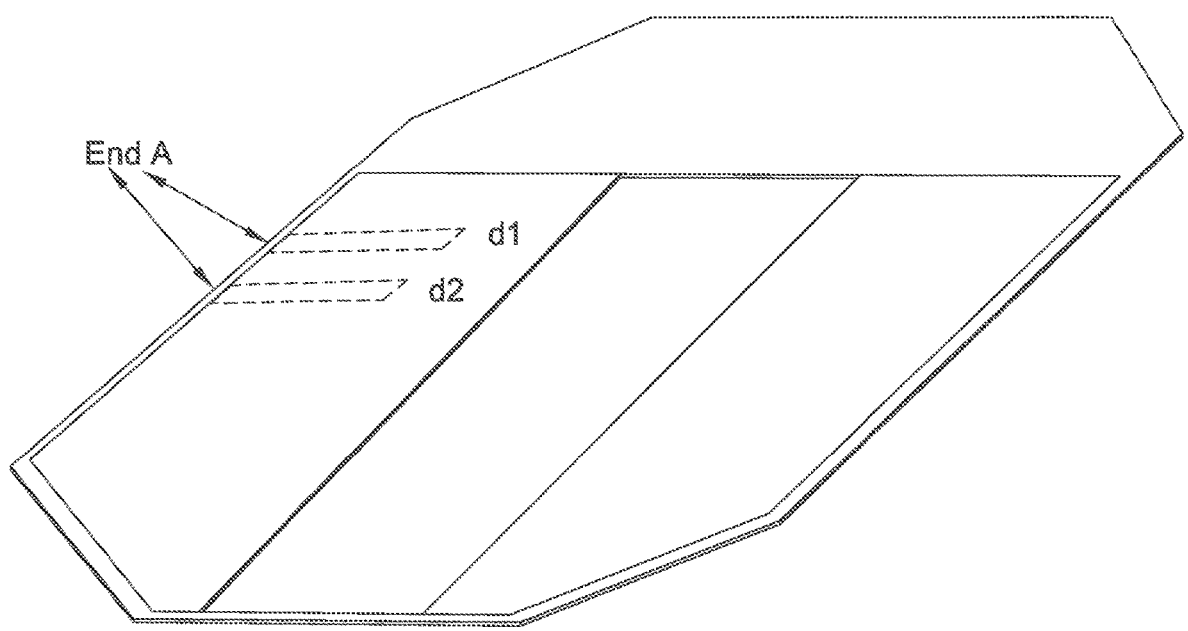
FIG. 17 is an illustration of a perspective view of an exemplary disposable flexible multi-panel sterilization assembly with barrier panel bolsters.

Samples S and T represent examples that demonstrate the invention and are illustrated in FIGS. 15 and 17 showing barrier panel bolsters extending from the side edges of the sterilization assembly towards the center. Samples P and Q represent comparative examples. Samples S and Q use the same types of nonwoven fabrics and have the same basis weights for their respective barrier panels. Samples P and Q are illustrated in FIGS. 14 and 16 showing reinforcing elements that do not extend to or adjacent the sides of the sterilization assembly.

The barrier panel bolsters of Sample S and the reinforcement elements of Sample Q are made from the same type of nonwoven fabrics and have the same basis weights. Likewise Samples T and P use the same types of nonwoven fabrics but have higher same basis weights for their respective barrier panels than Samples S and Q. The barrier panel bolsters of Sample T and the reinforcement elements of Sample P are made from the same type of nonwoven fabrics and have the same basis weights (but higher than those for Samples S and Q). It should be noted that the Samples S, T, P or Q were not subjected to steam or heat sterilization. The specific materials used for the samples are identified below. The properties are Average values are based on 10 specimens for each.

TABLE 1A

| Sample T | Single Ply Sterilization Wraps | Basis Weight | Frazier permeability | |
|---|---|---|---|---|
| | | | Average* | Standard Deviations, +/− |
| Bolster | KC600 | 2.57 osy (~86 gsm) | 25.99 | 1.395588 |
| Panel adjacent bolster | KC400 | 1.85 osy (~62 gsm) | 37.13 | 1.120565 |
| Panel not adjacent bolster | KC600 | 2.57 osy (~86 gsm) | 25.99 | 1.395588 |

TABLE 1B

| Sample P | Single Ply Sterilization Wraps | Basis Weight | Frazier permeability | |
|---|---|---|---|---|
| | | | Average* | Standard Deviations, +/− |
| Reinforcement elements | KC600 | 2.57 osy (~86 gsm) | 25.99 | 1.395588 |
| Panel adjacent reinforcement elements | KC400 | 1.85 osy (~62 gsm) | 37.13 | 1.120565 |
| Panel not adjacent reinforcement elements | KC600 | 2.57 osy (~86 gsm) | 25.99 | 1.395588 |

TABLE 1C

| Sample S | Single Ply Sterilization Wraps | Basis Weight | Frazier permeability | |
|---|---|---|---|---|
| | | | Average* | Standard Deviations, +/− |
| Bolster | KC200 | 1.20 osy (~40 gsm) | 66.44 | 3.13234 |
| Panel adjacent bolster | KC100 | 1.05 osy (~35 gsm) | 37.84 | 1.0469 |
| Panel not adjacent bolster | KC200 | 1.20 osy (~40 gsm) | 66.44 | 3.13234 |

TABLE 1D

| Sample Q | Single Ply Sterilization Wraps | Basis Weight | Frazier permeability | |
|---|---|---|---|---|
| | | | Average* | Standard Deviations, +/− |
| Reinforcement elements | KC200 | 1.20 osy (~40 gsm) | 66.44 | 3.13234 |
| Panel adjacent reinforcement elements | KC100 | 1.05 osy (~35 gsm) | 37.84 | 1.0469 |
| Panel not adjacent reinforcement elements | KC200 | 1.20 osy (~40 gsm) | 66.44 | 3.13234 |

For Sample S, the attachment of the barrier panel bolsters to the barrier panel is accomplished by:
discrete ultrasonically bonded points at the side edges of the panels; these attachment areas are included in specimens "a" (a1 and a2 as shown in FIG. 15), and conventional hot melt adhesive applied in an approximate 0.5 inch first stripe spaced approximately 2 inches away from the side edges and an approximate 0.5 inch second stripe spaced approximately 6.5 inches from the side edges; specimens "b" (b1 and b2 as shown in FIG. 15) contain some of the first stripe; the lack of hot melt between the stripes facilitates the passage of sterilant gas through the fabric layers.

The barrier panel bolster for Sample S is unattached between the first and second hot melt stripes; specimens "c" (c1 and c2 as shown in FIG. 15) lie between these stripes. The "a", "b" and "c" specimens were cut from the assembly as indicated in FIG. 15 and this corresponds to the "machine" Testing Direction given in the following table. A set of specimens was cut from the assembly as shown in FIG. 17; these are the "d" specimens (d1 and d2) and correspond to the "cross-machine" Testing Direction given in the following table.

Weight and drape stiffness averaged measurements for Sample S specimens are given in Table 2. The drape stiffness measurements conform to the Option A set-up arrangement per ASTM D1388-08.

TABLE 2

| Sample S Specimens | Construction | Testing Direction | Specimen average Wgt, gms per 1" × 8" strip | Specimen average length of overhang, cm | Specimen Drape Stiffness value, cm |
|---|---|---|---|---|---|
| c | panels + bolster no attachment | machine | 0.575 | 5.9 | 2.95 |
| b | panels + bolster with hot melt attachment | machine | 0.6745 | 12.6 | 6.3 |
| a | panels + bolster with ultrasonic attachment | machine | 0.575 | 15 | 7.5 |
| d | panels + bolster composite | cross-machine | 0.625 | 10 | 5 |

For Sample Q, the attachment of the reinforcement elements is accomplished utilizing a conventional hot melt adhesive applied substantially over the interfacing surface adjacent the contacting barrier panel. Specimens "b" (b1 and b2) and "c" (c1 and c2) contain the hot melt contribution. (The hot melt weight contribution is the difference with respect to Sample S's "c" specimen average weight value.) The panels are attached at the side edges utilizing the same ultrasonically bonded points as Sample S; specimens "a" (a1 and a2) for Sample Q contain only the barrier panels. The specimens sets of "a", "b" and "c" for Sample Q were cut as generally shown in FIG. 14, but their location with respect to the side edges was the same as Sample S; these specimens were cut to obtain "machine" Testing Direction values. The specimens for set "d" (d1 and d2) were cut as shown in FIG. 16 to give "cross-machine" Testing Direction values.

Weight and drape stiffness averaged measurements for Sample Q specimens are given in Table 3. The drape stiffness measurements conform to the Option A set-up arrangement per ASTM D1388-08.

TABLE 3

| Sample Q Specimens | Construction | Testing Direction | Specimen average Wgt, gms per 1" × 8" strip | Specimen average length of overhang, cm | Specimen Drape Stiffness value, cm |
|---|---|---|---|---|---|
| c | panels + reinforcement element with hot melt attachment | machine | 0.613 | 10.5 | 5.25 |
| b | panels + reinforcement element with hot melt attachment | machine | 0.6155 | 10.5 | 5.25 |
| a | panels with ultrasonic attachment | machine | 0.3815 | 14.2 | 7.1 |
| d | panels + reinforcement element composite | cross-machine | 0.515 | 7.55 | 3.775 |

For Sample T, the attachment of the barrier panel bolsters and the specimen specifics are essentially the same as for Sample S; the differences are in the respective fabric basis weights and overall dimensions (e.g. Sample T has larger barrier panels and barrier panel bolsters than S.) The relative location of the specimens from the side edges are the same. Table 4 gives the weight and drape stiffness averaged measurements for Sample T. The drape stiffness measurements conform to the Option A set-up arrangement per ASTM D1388-08.

TABLE 4

| Sample T Specimens | Construction | Testing Direction | Specimen average Wgt, gms per 1" × 8" strip | Specimen average length of overhang, cm | Specimen Drape Stiffness value, cm |
|---|---|---|---|---|---|
| c | panels + bolster no attachment | machine | 1.2315 | 13.5 | 6.75 |
| b | panels + bolster with hot melt attachment | machine | 1.4145 | 15.88 | 7.94 |
| a | panels + bolster with ultrasonic attachment | machine | 1.22 | 20.5 | 10.25 |
| d | panels + bolster composite | cross-machine | 1.2185 | 15.75 | 7.875 |

For Sample P, the attachment of the reinforcement elements and the specimen specifics (e.g. location with respect to the side edges, construction, and identification) is essentially the same as for Sample Q; the differences are in the respective fabric basis weights and overall dimensions (e.g. Sample P has larger barrier panels than Q.) Weight and drape stiffness averaged measurements for Sample P specimens are given in Table 5. The drape stiffness measurements conform to the Option A set-up arrangement per ASTM D1388-08.

TABLE 5

| Sample P Specimens | Construction | Testing Direction | Specimen average Wgt, gms per 1" × 8" strip | Specimen average length of overhang, cm | Specimen Drape Stiffness value, cm |
|---|---|---|---|---|---|
| c | panels + reinforcement element with hot melt attachment | machine | 1.22 | 15.2 | 7.6 |
| b | panels + reinforcement element with hot melt attachment | machine | 0.773 | 12.3 | 6.15 |
| a | panels with ultrasonic attachment | machine | 0.7535 | 16.8 | 8.4 |
| d | panels + reinforcement element composite | cross-machine | 0.8507 | 12.85 | 6.425 |

Thus, exemplary embodiments of the invention are presented herein; however, the invention may be embodied in a variety of alternative forms, as will be apparent to those skilled in the art. To facilitate understanding of the invention, and provide a basis for the claims, various figures are included in the description. The figures are not drawn to scale and related elements may be omitted so as to emphasize the novel features of the invention. Structural and functional details depicted in the figures are provided for the purpose of teaching the practice of the invention to those skilled in the art and are not intended to be considered limitations. Directional terms such as left, right, front or rear are provided to assist in the understanding of the invention and are not intended to be considered as limitations.

While particular embodiments of the present invention have been described herein; it will be apparent to those skilled in the art that alterations and modifications may be made to the described embodiments without departing from the scope of the appended claims.

What is claimed is:

1. A disposable flexible multi-panel sterilization assembly comprising:
   a barrier panel comprising a permeable sheet material having barrier properties, wherein the permeable sheet material is made from a thermoplastic polymer, the barrier panel including:
   a first surface and a second opposing surface,
   a first end:
   a flat pre-determined reference line, wherein the pre-determined reference line comprises printing, an imprint, or a combination thereof, wherein the pre-determined reference line aids in positioning of content to be sterilized,
   a second end opposite the first end,
   a first edge that is generally perpendicular to the pre-determined reference line,
   a second edge that is generally opposite the pre-determined reference line, and
   a third edge that is generally perpendicular to the pre-determined reference line, the barrier panel having a width that is measured from the first edge to the third edge and a length that is measured from the first end to the second end, the barrier panel having a midpoint along the length and extending between the first edge and the third edge to generally delineate the barrier panel into a content receiving region extending from the pre-determined reference line to the midpoint and a content covering region extending from the midpoint to the second edge;

barrier panel bolsters at or adjacent at least a portion of the first edge and third edge of the barrier panel, wherein said bolsters extend inwardly from said first and third edges and said bolsters increase the basis weight of the barrier panel by at least about 5 percent at or adjacent the edges of the barrier panel, wherein said bolsters comprise one or more layers of material bonded to the first surface or the second opposing surface of the barrier panel, further wherein attachment of the bolsters stiffens the barrier panel at or adjacent the edges of the barrier panel at least about 5 percent more than a stiffness of the bolsters and barrier panel when combined but unattached;

a panel attachment means between the pre-determined reference line and the midpoint of the barrier panel and at or near the first edge or the third edge; the panel attachment means being joined to the barrier panel at a pre-determined position to identify the content receiving region of the barrier panel and further to join the first edge of the barrier panel and third edge of the barrier panel to each other or to a portion of the content covering region after the barrier panel has been folded at or near the midpoint of the barrier panel such that the second end of the barrier panel is brought near the first end of the barrier panel; and a fold protection panel in juxtaposed communication with the barrier panel, the fold protection panel comprising a permeable sheet material, the fold protection panel including:

a proximal end generally adjacent the pre-determined reference line, a distal end generally opposite the proximal end; and at least a first edge and a second edge extending from the proximal end to the distal end, wherein the fold protection panel has a non-rectangular perimeter shape, the fold protection panel having a width at the proximal end that is measured from the first edge to the second edge at the proximal end and a length that is measured from the proximal end to the distal end, such that, after the barrier panel has been folded at or near the midpoint of the barrier panel so the second end of the barrier panel is brought near the first end of the barrier panel and the first and third edges of the barrier panel are joined to each other or to the content covering region to form a package, wherein the fold protection panel is configured to fold at or near the pre-determined reference line to cover at least the first edge and the third edge of the barrier panel when folded, wherein the barrier panel bolsters are configured to prevent the first and third edges of the barrier panel from folding back on the barrier panel during unfolding of the barrier panel.

2. The sterilization assembly of claim 1, wherein the barrier panel has a fourth edge.

3. The sterilization assembly of claim 2, wherein the barrier panel includes a fifth edge.

4. The sterilization assembly of claim 1, wherein the barrier panel bolsters prevent the barrier panel from folding back on itself during unfolding of the barrier panel after extended steam sterilization.

5. The sterilization assembly of claim 1, wherein the barrier panel bolsters are located in the content covering region at or adjacent the first and third edges of the barrier panel.

6. The sterilization assembly of claim 1, wherein the sterilization assembly further includes at least one pull tab attached to the second end of the barrier panel.

7. The sterilization assembly of claim 1, wherein the sterilization assembly further comprises indicia or instructions on the sterilization assembly for folding of the assembly into a package.

8. The sterilization assembly of claim 1, wherein the sterilization assembly further comprises indicia or instructions on the sterilization assembly for unfolding of the assembly after the assembly has been folded into a package and sterilized.

9. The sterilization assembly of claim 1, wherein said bolsters are bonded to the barrier panel by adhesive bonding, thermal bonding, ultrasonic bonding, bar sealing, or a combination thereof.

10. The sterilization assembly of claim 1, wherein the pre-determined reference line is provided on the barrier panel and barrier panel bolsters.

11. The sterilization assembly of claim 1, wherein the pre-determined reference line is an intermittent line printed or imprinted on the barrier panel.

12. The sterilization assembly of claim 1, wherein the fold-protection panel further comprises a third edge that is generally parallel to the pre-determined reference line.

13. A disposable flexible multi-panel sterilization assembly comprising:

a barrier panel having a first surface and a second opposing surface and comprising a sheet of barrier material, wherein the sheet of barrier material is made from a thermoplastic polymer, the sheet defining at least two panel edges, the barrier panel configured to be folded around content to be sterilized to form a package;

barrier panel bolsters at or adjacent at least a portion of at least two panel edges of the barrier panel, wherein said bolsters extend inwardly from said at least two panel edges and said bolsters increase the basis weight of the barrier panel by at least about 5 percent at or adjacent the at least two panel edges of the barrier panel, wherein said bolsters comprise one or more layers of material bonded to the first surface or the second opposing surface of the barrier panel, further wherein attachment of the bolsters stiffens the barrier panel at or adjacent the at least two panel edges of the barrier panel at least about 5 percent more than a stiffness of the bolsters and barrier panel when combined but unattached;

barrier panel attachment means located on a portion of the barrier panel for securing one or more panel edges of the barrier panel in a folded configuration around content to be sterilized, the barrier panel attachment means configured to secure the one or more panel edges in a folded configuration;

a flat pre-determined reference line present on the barrier panel, wherein the pre-determined reference line comprises printing, an imprint, or a combination thereof, wherein the pre-determined reference line aids in positioning of content to be sterilized;

a fold protection panel extending from the barrier panel, wherein the fold protection panel has a non-rectangular perimeter shape, the fold protection panel including:

a proximal end generally adjacent the barrier panel, a distal end generally opposite the proximal end; and wherein the distal end of the fold protection panel covers the at least two panel edges of the barrier panel after the barrier panel is in the folded configuration and further wherein the barrier panel bolsters are configured to prevent the at least two panel edges of the barrier panel from folding back on the barrier panel during unfolding of the barrier panel.

14. The sterilization assembly of claim 13, wherein the barrier panel bolsters prevent the barrier panel from folding back on itself during unfolding of the barrier panel after extended steam sterilization.

15. The sterilization assembly of claim 13, wherein the barrier panel bolsters comprise one or more layers of material selected from fibrous webs, textile webs, films and combinations thereof.

16. The sterilization assembly of claim 13, wherein the sterilization assembly further comprises indicia or instructions on the sterilization assembly for unfolding of the assembly after the assembly has been folded into a package and sterilized.

17. The sterilization assembly of claim 13, wherein said bolsters are bonded to the barrier panel by adhesive bonding, thermal bonding, ultrasonic bonding, bar sealing, or a combination thereof.

18. The sterilization assembly of claim 13, wherein the pre-determined reference line is provided on the barrier panel and barrier panel bolsters.

19. The sterilization assembly of claim 13, wherein the pre-determined reference line is an intermittent line printed or imprinted on the barrier panel.

20. The sterilization assembly of claim 13, wherein the fold-protection panel further comprises a third edge that is generally parallel to the pre-determined reference line.

* * * * *